United States Patent
Wang et al.

(10) Patent No.: US 9,201,078 B2
(45) Date of Patent: Dec. 1, 2015

(54) TSH IMMUNOASSAYS AND PROCESSES FOR PERFORMING TSH IMMUNOASSAYS IN THE PRESENCE OF ENDOGENOUS CONTAMINANTS IN RESTRICTED WASH FORMATS

(75) Inventors: Dan Wang, Kanata (CA); Gordon Bruce Collier, Fitzroy Harbour (CA); Joseph P. Skinner, Lake Villa, IL (US); Qiaoqiao Ruan, Kildeer, IL (US); Sergey Y. Tetin, Lindenhurst, IL (US)

(73) Assignee: Abbott Point of Care Inc., Princeton, NJ (US)

( * ) Notice: Subject to any disclaimer, the term of this patent is extended or adjusted under 35 U.S.C. 154(b) by 260 days.

(21) Appl. No.: 13/306,536

(22) Filed: Nov. 29, 2011

(65) Prior Publication Data

US 2012/0301905 A1 Nov. 29, 2012

Related U.S. Application Data

(60) Provisional application No. 61/491,088, filed on May 27, 2011.

(51) Int. Cl.
| | |
|---|---|
| G01N 33/543 | (2006.01) |
| G01N 33/74 | (2006.01) |
| G01N 33/76 | (2006.01) |
| C07K 16/26 | (2006.01) |
| C12M 3/00 | (2006.01) |
| B01L 3/00 | (2006.01) |
| G01N 33/53 | (2006.01) |

(52) U.S. Cl.
CPC ............ *G01N 33/76* (2013.01); *B01L 3/50273* (2013.01); *B01L 3/502738* (2013.01); *C07K 16/26* (2013.01); *G01N 33/5302* (2013.01); *G01N 33/543* (2013.01); *G01N 33/74* (2013.01); *C07K 2317/33* (2013.01); *G01N 2333/59* (2013.01)

(58) Field of Classification Search
CPC .......... B01L 3/50273; B01L 3/502738; C07K 16/26; C07K 2317/33; G01N 33/76; G01N 33/5302; G01N 33/543; G01N 2333/59; G01N 33/74
USPC ......... 422/401, 403, 408, 412, 414, 417, 425, 422/82.01; 435/7.94, 283.1, 285.2, 287.2, 435/287.9, 288.3, 288.4, 288.5; 436/501, 436/514, 518, 524, 525, 528, 534, 548; 530/388.24, 389.2, 391.1, 391.3
See application file for complete search history.

(56) References Cited

U.S. PATENT DOCUMENTS

| | | | |
|---|---|---|---|
| 4,722,889 A | 2/1988 | Lee et al. | |
| 5,026,653 A | 6/1991 | Lee et al. | |
| 5,096,669 A | 3/1992 | Lauks et al. | |
| 5,554,339 A | 9/1996 | Cozzette et al. | |
| 6,087,184 A | 7/2000 | Magginetti et al. | |
| 6,528,321 B1 | 3/2003 | Fitzgerald et al. | |
| 7,419,821 B2 | 9/2008 | Davis et al. | |
| 7,682,833 B2 | 3/2010 | Miller et al. | |
| 7,723,099 B2 | 5/2010 | Miller et al. | |
| 8,084,272 B2 | 12/2011 | Campbell et al. | |
| 2003/0170881 A1 | 9/2003 | Davis et al. | |
| 2004/0018577 A1 | 1/2004 | Campbell et al. | |
| 2008/0311676 A1 | 12/2008 | Brate et al. | |
| 2009/0065368 A1 | 3/2009 | Davis et al. | |
| 2009/0087869 A1* | 4/2009 | Fujimoto et al. | ............. 435/7.94 |
| 2009/0246800 A1* | 10/2009 | Mattingly et al. | ............. 435/7.1 |
| 2010/0112725 A1 | 5/2010 | Babu et al. | |
| 2010/0167301 A1 | 7/2010 | Collier et al. | |
| 2011/0117580 A1 | 5/2011 | Campbell et al. | |
| 2011/0290669 A1 | 12/2011 | Davis et al. | |

FOREIGN PATENT DOCUMENTS

| | | |
|---|---|---|
| CN | 101713779 A | 5/2010 |
| DE | 10337772 | 3/2005 |
| DE | 10341662 | 4/2005 |
| EP | 0768530 | 4/1976 |
| EP | 0 173 973 A2 | 3/1986 |
| EP | 0 212 522 A2 | 3/1987 |
| EP | 0915336 | 5/1999 |
| WO | WO 96/27129 | 9/1996 |
| WO | WO 00/51814 | 9/2000 |
| WO | WO 02/01229 | 1/2002 |
| WO | WO 03/076937 | 9/2003 |

OTHER PUBLICATIONS

U.S. Appl. No. 61/371,066, filed Aug. 5, 2010, Miller.
Wu, "A selected history and future of immunoassay development and applications in clinical chemistry", Clinica Chimca Acta, vol. 369, Issue 2, Jul. 31, 2006, pp. 119-124.
Engel et al., "Cedia in vitro diagnostics with a novel homogeneous immunoassay technique: Current status and future prospects", Journal of Immunological Methods, vol. 150, Issues 1-2, Jun. 24, 1992, pp. 99-102.
Vassart et al., "A molecular dissection of the glycoprotein hormone receptors", Trends in Biochemical Sciences, vol. 29, Issue 3, Mar. 2004, pp. 119-126.
Wada et al., "Enzyme Immunoassay of the Glycoprotein Tropic Hormones—Choriogonadotropin, Lutropin, Thyrotropin- with Solid-Phase Monoclonal Antibody for the α-Subunit and Enzyme-Coupled Monoclonal Antibody Specific for the β-Subunit", CLin. Chem. 28/9, 1862-1866 (1982) (5 Pages).

(Continued)

*Primary Examiner* — Gail R Gabel
*Assistant Examiner* — James L Grun

(57) ABSTRACT

The invention relates to low wash Thyroid Stimulating Hormone (TSH) immunoassays using an ELISA sandwich assay having limited or no wash step between the antigen capture, detection antibody addition and substrate introduction steps. This invention exhibits low cross reactivity with biologically similar interfering cross reacting species, such as Follicle Stimulating Hormone (FSH), Luteinizing Hormone (LH) and Chorionic Gonadotropin (CG).

14 Claims, 8 Drawing Sheets

(56) References Cited

OTHER PUBLICATIONS

Cornell et al., "The Subunits of Human Pituitary Thyroid-stimulating Hormone: Isolation, Properties, and Composition", The Journal of biological Chemistry, vol. 248, No. 12, Issue of Jun. 25, pp. 4327-4333, 1973 (7 pages).
Inoue et al., "Highly Specific and Sensitive Sandwich Enzyme Immunoassay for Human Thyroid-Stimulating Hormone (hTSH) β-Subunit Fab'-Horseradish Peroxidase Conjugate", Analytical Letters, vol. 19, Issue 9-10, 1986, pp. 121-1136.
Soos et al., "A rapid, sensitive two-site immunometric assay for TSH using monoclonal antibodies: Investigation of factors affecting optimisation", Journal of Immunological Methods, vol. 73, Issue 2, Oct. 26, 1984, pp. 237-249.
Lode et al., "One-step quantitative thyrotropin assay for the detection of hypothyroidism in point-of-care conditions", Clinical Biochemistry, vol. 36, Issue 2, Mar. 2003, pp. 121-128.
Ruan et al., "Using nonfluorescent Förster resonance energy transfer acceptors in protein binding studies", Analytical Biochemistry, vol. 393, Issue 2, Oct. 15, 2009, pp. 196-204.
International search Report and Written Opinion for PCT/US2011/062452 dated Feb. 27, 2012.
P. Huhtinen, "Quantitative, Rapid Europium (III) Nanoparticle-Label-Based-All-In-One Dry-Reagent Immunoassay for Thyroid-Stimulating Hormone", Clinical Chemistry, vol. 50, No. 10, Oct. 1, 2004, pp. 1935-1936.
"Anti-h TSH 5409 SPTNE-5", MedixMab, May 12, 2010.
"Anti-h TSH 5405 SP-1", MedixMab, May 12, 2010.
"Anti-h TSH 5404 SP-1", Sep. 20, 2010.
Ylikotila et al., "A sensitive TSH assay in spot-coated microwells utilizing recombinant antibody fragments", Journal of Immunological Methods, vol. 306, No. 1-2, Nov. 30, 2005, pp. 104-114.
Fitzgerald, "Matched-Pair Components and Related Products", Fitzgerald Industries International, Apr. 8, 2009.
Karlsson, "Determination of antibody affinity and kinetic binding constants in Gyrolab Bioaffy microfluidic CD", Jan. 1, 2008.
Office Action for U.S. Appl. No. 13/306,712 dated Sep. 17, 2012.
Tanaka, et al., "Improved methods for detecting beta-core in normal and cancer patient urines", Clinical Chemistry, vol. 40, No. 12, Jan. 1, 1994, pp. 2317-2318.
Cheng, et al., "Automated on-line microdialysis sampling coupled with high-performance liquid chromatography for simultaneous determination of malondialdehyde and oflaxin in whole blood", Talanta, Elsevier, Amsterdam, vol. 79, No. 4, Sep. 15, 2009, pp. 1071-1075.
International Search Report and Written Opinion for PCT/US2011/062450 mailed Feb. 27, 2012.
International Search Report and Written Opinion for PCT/US2011/062456 mailed Mar. 9, 2012.
International Preliminary Report on Patentability for PCT/US2011/062452 mailed Dec. 12, 2013.
First Office Action mailed Dec. 12, 2014 in CN Patent Application No. 201180072165.4, 17 pages.
Nareoja, T. et al. (2009, e-pub. Jun. 6, 2009). "Impact of Surface Defects and Denaturation of Capture Surface Proteins on Nonspecific Binding in Immunoassays Using Antibody-coated Polystyrene Nanoparticle Labels." *Journal of Immunological Methods* 347:24-30.
European Office Action mailed on Aug. 6, 2015 for EP Patent Application No. 11 793 964.5, 6 pages.
European Office Action mailed on Aug. 7, 2015 for EP Patent Application No. 11 793 965.2, 5 pages.

\* cited by examiner

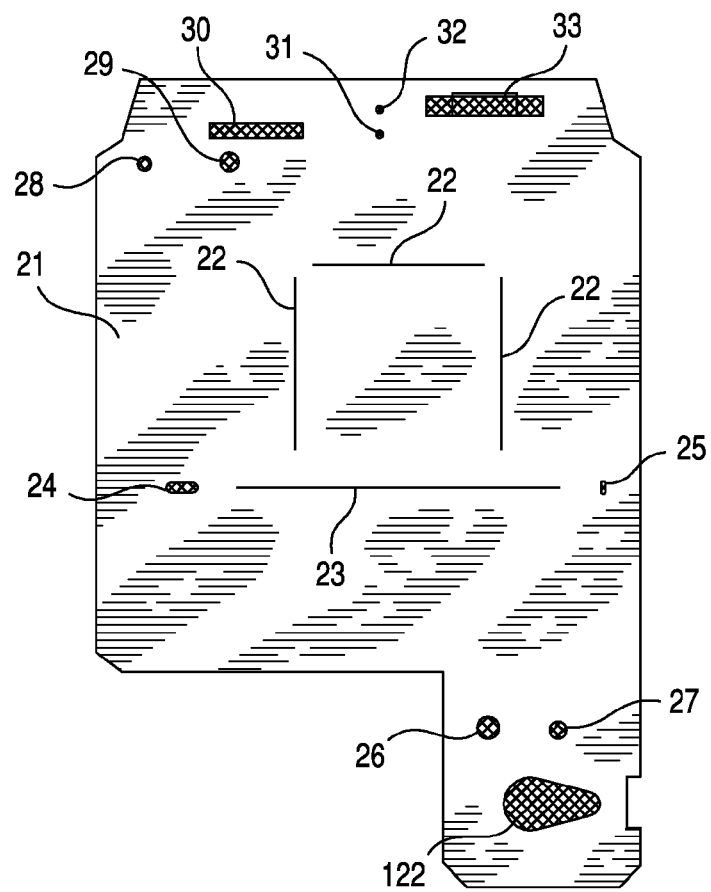
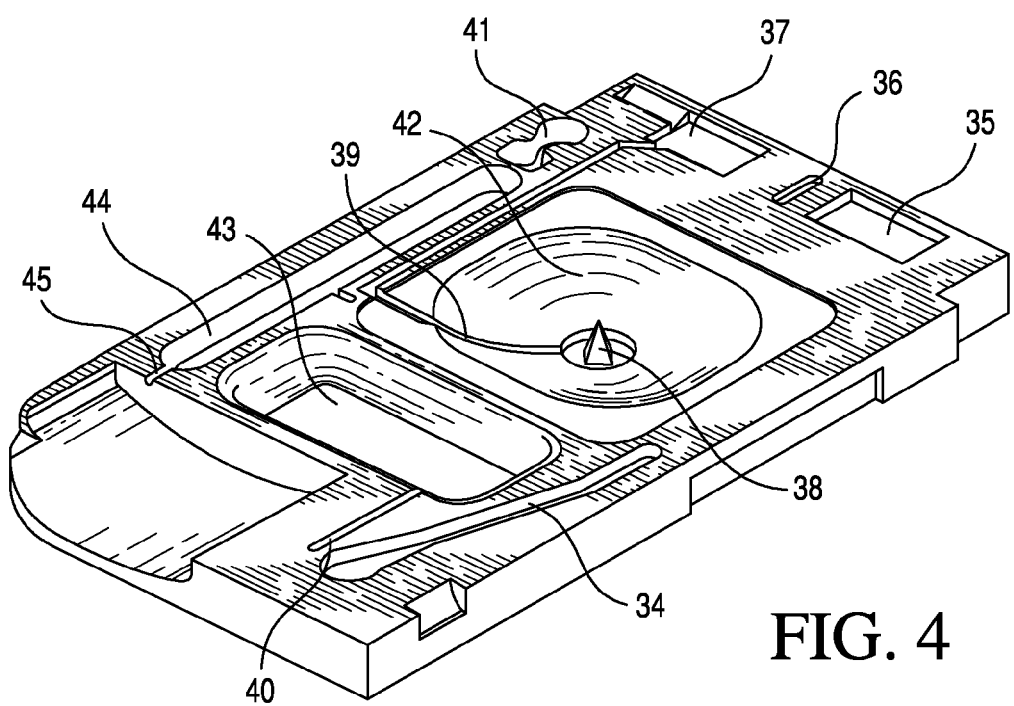

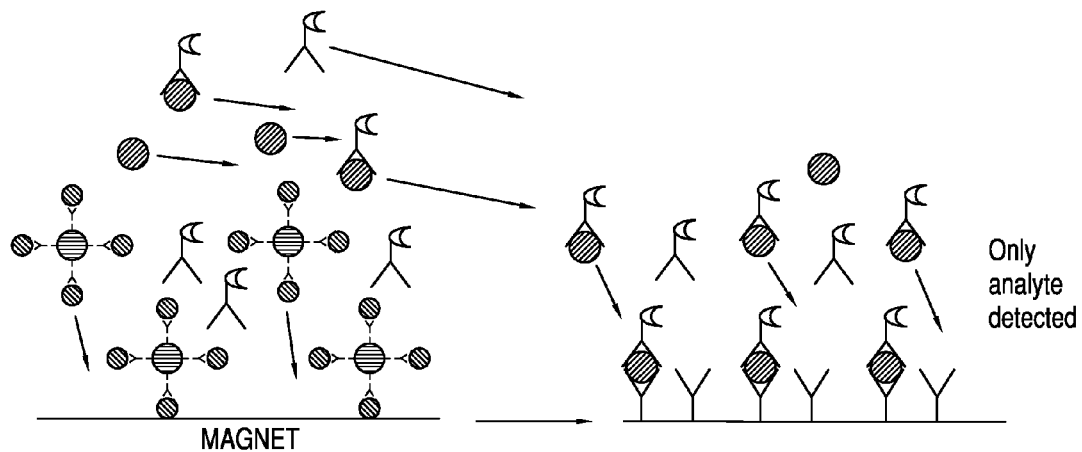
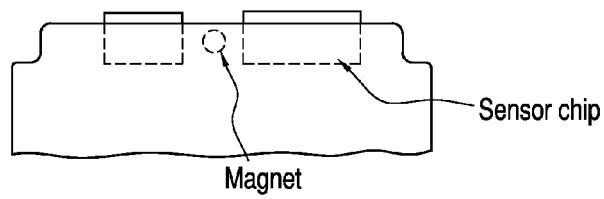
- Y Capture Ab
- Y' Scavenger MAb
- ⚡ Label
- ◉ TSH antigen
- ◉ Cross reactant
- ⊖ Magnetic Beads
FIG. 8

TSH IMMUNOASSAYS AND PROCESSES FOR PERFORMING TSH IMMUNOASSAYS IN THE PRESENCE OF ENDOGENOUS CONTAMINANTS IN RESTRICTED WASH FORMATS

CROSS REFERENCE TO RELATED APPLICATIONS

The present invention claims priority to U.S. Provisional Application No. 61/491,088, filed on May 27, 2011, the entire contents and disclosure of which are hereby incorporated by reference.

FIELD OF THE INVENTION

This invention relates generally to methods of performing an immunoassay in systems having minimal washing capabilities. In particular, this invention relates to methods of performing a Thyroid Stimulating Hormone (TSH) assay in the presence of its related contaminating (cross-reacting) endocrine glycoprotein hormone analogues. The invention also relates to processes for selecting antibodies with the best performance characteristics for performing TSH assays. These assays also benefit from the inclusion of scavenging reagents that further ameliorate the effect of interfering substances such as the endocrine glycoprotein hormone analogues.

BACKGROUND OF THE INVENTION

Immunoassays, first developed in 1959, have become useful sensitive diagnostic tools for human and veterinary health, and environmental testing (Wu, 2006, Clinica Chimica Acta, 369:119). Their application has become ubiquitous and well known in the art.

There are several approaches to perform immunoassays, and this invention focuses on non-competitive or sandwich immunoassays. Immunoassays can also be categorized as heterogeneous or homogeneous. Homogeneous assays have simpler assay characteristics, but have been limited to high concentration drugs (Engel & Khanna, 1992, Journal of Immunological Methods, 150:99). Heterogeneous assays require the separation of bound material from unbound material and are the focus of the present invention.

Sandwich immunoassays are typically performed as two step assays involving first the introduction of an antigen-containing sample to a capture antibody or antibodies covalently attached to a solid support. This is followed by washing away non-specific sample components, leaving the antigen of interest bound to the solid support antibody. In a second step, a detection or signal antibody is introduced into the assay, followed by another wash step. Lastly, the detection substrate is added to the assay to quantify the antigen concentration. Two step immunoassays with associated wash steps are generally preferred as they reduce background signal permitting highly sensitive detection.

A "one step" sandwich immunoassay may be performed by introducing the detection antibody and antigen containing sample together to a capture antibody or antibodies covalently attached to a solid support. The resulting assay is washed to remove unbound reagents. Lastly, the detection substrate is added to the assay to quantify the antigen concentration.

The need exists for one step assays with limited wash fluid volume, as they are simpler and require fewer steps and fewer associated hardware complexities in order to operate, particularly in point-of-care applications. For point-of-care devices, the reducing or eliminating the need for a wash step reduces device cost and assay time, hardware cost and complexity, and disposable device size, which in turn is of benefit to reducing waste in the environment, as well as its cost.

To date, one step immunoassays with limited or no wash steps have not been used for antigens where the presence of endogenous related antigens create high backgrounds that confound detection results. This is particularly true when the endogenous antigens are found at high molar concentrations in excess of the antigen of interest, which is common for some disease conditions.

An example of a problematic antigen is thyroid stimulating hormone (TSH), also known as thyrotropin, which is typically present in combination with the related endocrine glycoprotein hormones chorionic gonadotropin (CG), luteinizing hormone (LH), and follicle stimulating hormone (FSH). These four related hormones have an identical alpha subunit and a highly similar beta subunit (Vassart, 2004, Trends in Biochemical Sciences, 29(3):119). Consequently, antibodies against the alpha subunit do not discriminate between these four hormones (Wada, 1982, Clinical Chemistry, 28(9):1862). It is also difficult to identify beta-specific antibodies that can discriminate amongst the four related hormones, particularly in the presence of very high concentrations of contaminating hormones, as these hormones have very similar primary sequences (Cornell, 1973, The Journal of Biological Chemistry, 248(12):4327). Further, it is difficult to identify unique (antigenic) epitopes on TSH and to obtain antibodies that recognize these unique epitopes. For sandwich assays, it is also important to employ capture and signal antibodies that do not overlap having the appropriate specificity characteristics, further limiting the choice of antibodies.

Wash steps in sandwich immunoassays help to reduce the concentration of contaminating hormones in the reaction, which reduces the signal associated with the contaminating species. Therefore, one step sandwich immunoassays with no wash step or limited wash capabilities have been unable to specifically detect TSH in the presence of the related contaminating hormone molecules, especially when the contaminants are present at very high concentrations. See, e.g., US20080311676, which describes the importance of using a wash step in an immunoassay to reduce the concentration of cross-reacting species. Attempts to address these problems can be found in Hashida et al. 1986, Analytical Letters, 19, 1121-36; Soos et al., 1984, Journal of Immunological Methods, 73, 237; and Lode et al., 2003 Clinical Biochemistry, 36, 121.

EP 173973 describes a method for the determination of TSH, in which an anti-β-subunit TSH monoclonal antibody having a specific association constant value is used. Related EP 212522 describes an assay characterized in that TSH-β subunit specific monoclonal antibodies recognize different epitopes. This method seeks to reduce inhibition by the presence of other glycoprotein hormones such as LH, CG and FSH.

The need exists for one step sandwich immunoassays, particularly those used for point-of-care assays, having reduced or eliminated wash capabilities, and in particular to one step sandwich immunoassays for detecting TSH. In addition, the need exists for identifying antibody reagents capable of performing such immunoassays.

SUMMARY OF THE INVENTION

The present invention relates to devices, immunoassays and methods for detecting thyroid stimulating hormone (TSH) in a fluid sample, while minimizing interference caused by the highly related endogenous endocrine glycoprotein hormones, Follicle Stimulating Hormone (FSH), Luteinizing Hormone (LH), and Chorionic gonadotropin (CG).

In one embodiment, the invention is to a thyroid stimulating hormone (TSH) sandwich immunoassay, comprising at least two epitope-compatible antibodies comprising at least one capture antibody and at least one signal antibody, wherein the dissociation constant (Kd) of both antibodies for TSH is less than or about 1 nM, e.g., no greater than 0.5 nM or no greater than 0.15 nM, and wherein the capture antibody Kd for: follicle stimulating hormone (FSH) is greater than 1000 nM, greater than 2500 nM or greater than 3000 nM; luteinizing hormone (LH) is greater than 500 nM, greater than 1000 nM or greater than 3000 nM; and chorionic gonadotropin (CG) is greater than 200 nM, greater than 500 nM or greater than 2500 nM, and wherein the immunoassay uses a single wash step.

In another embodiment, the invention is to a method for performing a TSH immunoassay, the method comprising the steps of: (a) inserting a fluid sample into a device comprising an immunosensor in a conduit, said immunosensor having a capture antibody to TSH; (b) dissolving a signal antibody into said fluid sample; (c) forming a sandwich complex on said immunosensor, said complex comprising said capture antibody, TSH, and said signal antibody; (d) washing uncomplexed signal antibody from the sensor with a wash fluid in no more than one washing step; and (e) detecting a signal associated with said complexed signal antibody. Preferably, the capture antibody and the signal antibody each have a dissociation constant (Kd) for TSH of no greater than 1 nM, no greater than 0.5 nM, or no greater than 0.15 nM. The sandwich complex preferably is formed by substantially non-sequential contact of said capture and signal antibodies with the fluid sample. The sandwich complex preferably is formed without one or more intervening wash steps directed to ameliorating a cross reaction with one or more of FSH, LH and CG. The method preferably comprises a single wash step to remove sample and unbound signal antibody from the capture antibody and where the wash fluid also comprises a substrate for a reporter molecule. The method may further comprise a step of metering the fluid sample in a metering chamber to form a metered sample having a volume of from 1 to 500 µL. Optionally, the method comprises a step of bursting a wash fluid pouch, which is in fluid communication with the immunosensor, to release from 5 to 500 µL of wash fluid into said conduit. A plurality of air segments optionally may be formed in the wash fluid to facilitate washing of the immunoassay.

In another embodiment, the invention is to a TSH sandwich immunoassay antibody selection method for non-sequential assays and assays with low wash fluid cycles, comprising selecting at least two epitope-compatible antibodies comprising at least one capture antibody and at least one signal antibody, wherein the capture antibody dissociation constant (Kd) for TSH is less than about 1 nM, less than 0.5 nM or less than 0.15 nM, and wherein the capture antibody Kd value for FSH is greater than 1000 nM, greater than 2500 nM or greater than 3000 nM, for LH is greater than 500 nM, greater than 1000 nM or greater than 3000 nM, and for CG is greater than 200 nM, greater than 500 nM or greater than 2500 nM, and wherein the signal antibody Kd for TSH is less than about 1 nM, less than 0.5 nM or less than 0.15 nM, and the signal antibody Kd for FSH is greater than 250 nM or greater than 1000 nM, for LH is greater than 35 nM, greater than 200 nM or greater than 250 nM, and for CG is greater than 35 nM or greater than 250 nM.

In a preferred aspect, the signal antibody Kd for FSH is preferably greater than 250 nM or greater than 1000 nM, for LH preferably is greater than 35 nM, greater than 200 nM or greater than 250 nM, or greater than 1000 nM, and for CG preferably is greater than 35 nM or greater than 250 nM. Optionally, the capture antibody Kd value for FSH is preferably greater than 1000 nM, preferably greater than 2500 nM or greater than 3000 nM, for LH is greater than 500 nM, greater than 1000 nM or greater than 3000 nM, and for CG is preferably greater than 200 nM, greater than 500 nM or greater than 2500 nM. In terms of ranges, the capture antibody optionally has a Kd(FSH) of from 1000 to 5000 nM, a Kd(LH) of from 500 to 5000 nM, and a Kd(CG) of from 200 to 5000 nM, and the signal antibody preferably has a Kd(FSH) of from 250 to 5000 nM, a Kd(LH) of from 200 to 5000 nM, and a Kd(CG) of from 35 to 5000 nM. More preferably the capture antibody has a Kd(LH) of from 1000 to 5000 nM and a Kd(CG) of from 500 to 5000 nM, and more preferably the signal antibody has a Kd(LH) of from 35 to 5000 nM. The fluid sample employed preferably comprises a diluted blood sample, an undiluted blood sample, a diluted plasma sample, or an undiluted plasma sample.

The capture antibody and the signal antibody, respectively, preferably are capable of binding to at least two different epitopes on the TSH-β subunit of TSH. Thus, the capture antibody and the signal antibody preferably are epitope-compatible antibodies. In a particularly preferred embodiment, the capture antibody and signal antibody are selected from the following capture/signal antibody pairs 5409/T25C and T25C/5409. The capture antibody, for example, may comprise mouse monoclonal antibody (Biospacific Cat#5409 SPTNE-5) and the signal antibody may comprise mouse monoclonal antibody (Fitzgerald Cat#10-T25C).

In one aspect, the capture antibody has a first Kd ratio, Kd(FSH):Kd(TSH), of greater than 2500, e.g., greater than 3000, and the signal antibody has a second Kd ratio, Kd(FSH):Kd(TSH), of greater than 1500, e.g., greater than 1800. Optionally, the first Kd ratio ranges from 1500 to 50000, and the second Kd ratio ranges from 1500 to 50000. More preferably, the capture antibody has a first Kd ratio, Kd(FSH):Kd(TSH), of greater than 6000.

BRIEF DESCRIPTION OF THE DRAWINGS

The present invention will be better understood in view of the following non-limiting figures.

FIG. 3 is a top view of the layout of a tape gasket for an immunosensor cartridge;

FIG. 4 is an isometric top view of an immunosensor cartridge base;

FIG. 8 illustrates magnetic bead capture of FSH and LH;

DETAILED DESCRIPTION OF THE INVENTION

Introduction

Figure 1:
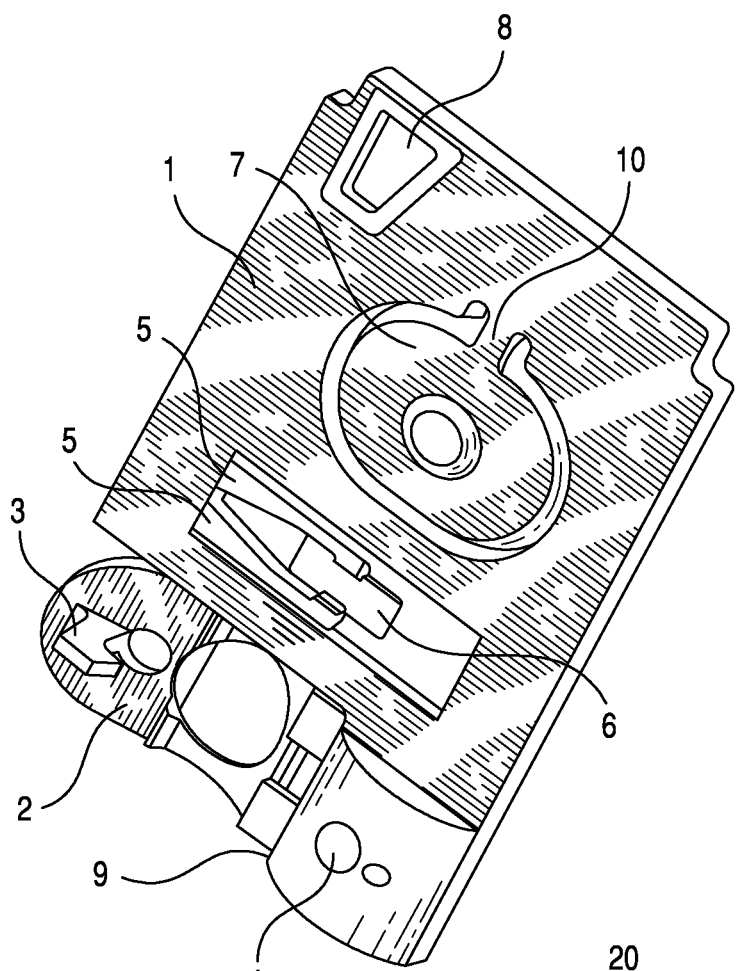
FIG. 1 is an isometric top view of an immunosensor cartridge cover.

In various embodiments, the present invention relates to immunoassays, devices and methods for performing sandwich Enzyme Linked Immunosorbent Assays (ELISAs) in the presence of interfering substances, preferably with limited or no wash step. The invention beneficially permits accurate assay results in the presence of these contaminating interfering substances. In a first embodiment, the present invention relates to devices and methods for conducting thyroid stimulating hormone (TSH) sandwich immunoassays as well as methods for selecting antibodies for such immunoassays. In a second embodiment, the invention relates to immunoassays, in particular to TSH immunoassays, and to associated devices and methods that employ a single wash step or no wash step. In a third embodiment, the invention relates to immunoassays, in particular to TSH immunoassays, and associated devices and methods that employ scavenger beads coated with antibodies to endogenous contaminants that reduce or eliminate interference associated with such contaminants. Alternatively, such antibodies may be covalently bound to the cartridge surface or may comprise free antibodies in the reaction medium. Optionally, one or more of these embodiments may be combined with one another.

TSH Immunoassays and Methods for Selecting Antibodies for TSH Immunoassays

In the first embodiment, the invention relates to immunoassays for TSH and to related devices and methods for conducting such immunoassays. The inventive immunoassays beneficially provide for the accurate detection of TSH notwithstanding the presence of the highly related endogenous endocrine glycoprotein hormones, Follicle Stimulating Hormone (FSH), Luteinizing Hormone (LH), and Chorionic gonadotropin (CG). In certain disease states, these related hormones may be present at significantly high concentrations. The assay is illustrated herein with respect to the i-STAT® immunoassay platform (Abbott Point of Care Inc., Princeton, N.J., USA), which is a low wash volume platform. See jointly owned U.S. Pat. No. 7,419,821, the entirety of which is incorporated herein by reference. In the present specification, the term "low wash" is taken to include unitized disposable test devices that incorporate a pouch with a relatively small amount of wash fluid, typically on the order of a few tens of microliters up to about five milliliters, or similar devices where a similar amount of wash fluid is delivered from an instrument with which the device is engaged. In some exemplary embodiments, the device and method employ a wash volume of from 5 to 500 μL, e.g., from 25 to 250 μL, or from 50 to 150 μL, preferably about 100 μL. It also includes the concept of an assay where the capture antibody, analyte and signal antibody are mixed together to form the sandwich immunoassay and then the wash fluid is used to remove sample with unbound analyte and unbound signal antibody from the sandwich that is formed on the capture antibody, which preferably is in some way immobilized, e.g., on a bead that may be magnetic or on a sensor. These types of devices and systems are generally associated with testing at the point of patient care.

In another aspect, the invention relates to a method of selecting antibodies for performing a sandwich ELISA assay in a system with limited wash capabilities. Specifically, antibodies are selected that have reduced cross-reactivity, which in turn increases analytical specificity in a sandwich ELISA. These characteristics are particularly useful for low-wash sandwich ELISA assays. As a specific example, the performance of a TSH assay using an i-STAT® cartridge in the presence of the endogenous endocrine glycoprotein hormones, FSH, LH and CG, is demonstrated herein. By contrast, typical prior commercial systems assaying TSH utilize a plurality of wash steps to reduce the presence of the endogenous endocrine glycoprotein hormones which can be present at high molar concentrations under certain disease conditions. However, it is apparent that these multiple wash systems would also benefit from the use of antibodies with these specificity characteristics disclosed in the present specification, and the present invention should not be considered limited to immunoassay systems or devices that employ limited wash capabilities.

In a preferred embodiment, the two sandwich antibodies are selected against primarily the beta-subunit of the TSH molecule or an epitope overlapping with this region exhibiting the desired degree of specificity. Ideal characteristics of these two sandwich antibodies are that they recognize epitopes (preferably different epitopes) of the beta-subunit of TSH and not exclusively the alpha-subunit of TSH. It is contemplated that this recognition could involve an epitope spanning both the alpha and beta subunits that exhibits high affinity to TSH and low affinity for the other cross-reacting species. Furthermore, these antibodies preferably exhibit a low Kd for the TSH molecule, while having a high Kd value for the other endogenous glycoprotein hormones, FSH, LH and CG.

As used herein, the term "dissociation constant" or "Kd" refers to the equilibrium constant for the general reaction:

$$A + B \underset{k_{-1}}{\overset{k_1}{\rightleftharpoons}} AB$$

where A is an antibody and B is an analyte, i.e., antigen. For this reaction, the dissociation constant or Kd value may be expressed as:

$$Kd = \frac{[A] \times [B]}{[AB]} = \frac{k_{-1}}{k_1}$$

Generally, the lower the dissociation constant, the greater the affinity or degree of binding antibody A has for analyte B. Methods of determining these kinetic values are well known in the art. See, e.g., Goodrich & Kugel, 2007, Binding and Kinetics for Molecular Biologists, Cold Spring Harbour Laboratory Press, Cold Spring Harbour, N.Y.

In a particularly preferred embodiment, the capture and signal antibodies exhibit a high affinity (low Kd) for TSH. Antibodies that generate poor signal at low concentrations will have high variability (noise) and will be difficult to discriminate from higher measured cross-reactivity. These antibodies should not be selected as candidate antibodies. In a particularly preferred embodiment, antibodies having a Kd for TSH antigen of no greater than 1 nM, e.g., no greater than 0.5 nM, no greater than 0.15 nM, or no greater than 0.1 nM, are selected to act as the capture and/or signal antibodies for the immunoassays of the present invention.

In another preferred embodiment for the two or more antibodies selected for a sandwich hybridization, the antibody having the greatest Kd values for FSH, LH, and CG will be used as the capture antibody. In another aspect, if two antibodies are identified as candidates for the capture and signal antibodies, the antibody having the greater Kd value (e.g., from 5 to 1000% greater, from 20 to 100% greater or from 20 to 50% greater) may be preferred as the capture antibody. In either case, in addition to having a low Kd value for TSH, e.g., no greater than 1 nM, no greater than 0.5 nM, no greater than 0.15 nM, or no greater than 0.1 nM, it is desirable that the antibodies (capture and signal antibodies) have relatively high Kd values for each of the interfering endocrine glycoprotein hormones, FSH, LH and CG.

In a particularly preferred embodiment, the capture antibody has a Kd (FSH) greater than 1000 nM, greater than 2500 nM, greater than 3000 nM or greater than 4000 nM, a Kd (LH) greater than 500 nM, greater than 800 nM, greater than 1000 nM, greater than 2500 or greater than 4000 nM, and a Kd (CG) greater than 200 nM, greater than 500 nM, greater than 2500 nM or greater than 4000 nM. In terms of ranges, the capture antibody optionally has a Kd (FSH) ranging from 1000 to 5000 nM, from 1500 to 4000 nM or from 2500 to 3000 nM, a Kd (LH) ranging from 500 to 5000 nM, from 750 to 1200 nM, from 800 to 1000 nM, from 1000 to 5000 or from 1500 to 4000 nM, and a Kd (CG) ranging from 35 to 5000 nM, from 200 to 5000 nM, from 210 to 2500 nM or from 220 to 500 nM.

Similarly, the signal antibody preferably has a Kd (FSH) that is greater than 250 nM, greater than 1000 nM or greater than 4000 nM, a Kd (LH) that is greater than 35 nM, greater than 200 nM, greater than 250 nM, greater than 1000 nM, greater than 2500 nM or greater than 4000 nM, and a Kd (CG) that is greater than 35 nM, greater than 250 nM or greater than 2500 nM. In terms of ranges, the signal antibody optionally has a Kd (FSH) ranging from 250 to 5000 nM, from 250 to 2500 nM or from 250 to 500 nM, a Kd (LH) ranging from 35 to 5000, from 200 to 5000 nM, from 35 to 2500 nM, from 200 to 2500 nM, from 35 to 1000 nM or from 200 to 1000 nM, and a Kd (CG) ranging from 35 to 5000 nM, from 35 to 2500 nM or from 35 to 1000 nM. In specific embodiments of this method, the TSH binding species preferably are selected from an antibody, a fragment of an antibody (e.g., Fab fragment), a single chain antibody, aptamers, receptors and other specific binding species.

A preferred embodiment of the present invention addresses a TSH sandwich immunoassay comprising at least two epitope-compatible antibodies comprising at least one capture antibody and at least one signal antibody, wherein the Kd of both antibodies for TSH is less than (or no greater than) about 1 nM, e.g., no greater than 0.5 nM, no greater than 0.15 nM, or no greater than 0.1 nM, and wherein the capture antibody Kd for FSH, LH and CG are greater than about 2500, greater than about 500 and greater than about 200 nM, respectively, and wherein the signal antibody Kd for FSH, LH and CG are greater than about 250, greater than about 200, and greater than about 35 nM, respectively. More preferably, the capture antibody Kd for CG is greater than about 35 nM and the signal antibody Kd for LH is greater than about 35 nM. In this context, by "epitope compatible" it is meant that the antibodies can selectively bind to different epitopes on the analyte of interest, as discussed above. For TSH immunoassays, the antibodies preferably can selectively bind to different epitopes that are, at least in part, on the beta-subunit of TSH.

The relative selectivity of the capture and signal antibodies for TSH over FSH, LH and CG may also be characterized in terms of a Kd ratio, i.e., the ratio of Kd(endocrine glycoprotein hormone analogue, e.g., FSH, LH, CG or an average thereof):Kd(TSH). In this aspect, the larger the Kd ratio value, the greater the ability of the antibody to selectively bind to TSH over the endocrine glycoprotein hormone analogue in the denominator. In one aspect, for example, the immobilized antibody has a first Kd ratio, $Kd_{FSH}:Kd_{TSH}$, of greater than 2500, e.g., greater than 3000 or greater than 5000. Additionally or alternatively, the signal antibody may have a second dissociation constant ratio, $Kd_{FSH}:Kd_{TSH}$, of greater than 1500, e.g., greater than 1800 or greater than 2000. In terms of ranges, the immobilized antibody preferably has a first Kd ratio, $Kd_{FSH}:Kd_{TSH}$, of from 1500 to 50000, e.g., from 1800 to 30000 or from 2000 to 28000, and the signal antibody may have a second Kd ratio, $Kd_{FSH}:Kd_{TSH}$, of from 1500 to 50000, e.g., from 1800 to 30000 or from 1900 to 20000.

As discussed above, the immunoassay preferably employs a pair of different antibodies that bind to TSH at two non-overlapping epitopes. In a particularly preferred embodiment, the capture antibody comprises a TSH capture mouse monoclonal antibody (e.g., Biospacific Cat#5409 SPTNE-5) and the signal antibody comprises a signaling mouse monoclonal antibody (e.g., Fitzgerald Cat#10-T25C). In this aspect, the capture antibody preferably is covalently bound to beads, e.g., latex and/or polystyrene beads, and the signal antibody is conjugated to a reporter molecule selected from the group consisting of alkaline phosphatase, horseradish peroxidase and a fluorescent or optically absorbing moiety. The detection step is preferably electrochemical, e.g., amperometric, but can also be optical, e.g., fluorescence and absorbance.

The present invention may also be characterized as a ligand binding assay. For example, in one embodiment, the invention is to a TSH sandwich assay comprising at least one capture ligand and at least one signal ligand, wherein the dissociation constant of both ligands for TSH is less than (or no greater than) about 1 nM, e.g., no greater than 0.5 nM, no greater than 0.15 nM, or no greater than 0.1 nM, and wherein the capture ligand Kd for FSH, LH and CG are greater than about 2500, greater than about 500 and greater than about 200 nM, respectively, and wherein the signal ligand Kd for FSH, LH and CG are greater than about 250, greater than about 200 and greater than about 35 nM, respectively. More preferably, the capture ligand Kd for LH is greater than about 1000 nM and for CG is greater than about 500 nM, and the signal ligand Kd for LH is greater than about 35 nM. Here, the ligands may be selected from the group consisting of monoclonal antibodies, polyclonal antibodies, fragments of an antibody, aptamers and single chain antibodies.

The invention is also directed to methods for detecting an analyte, e.g., TSH, with an immunoassay that is highly selective for TSH and that is non-selective for competing endocrine glycoprotein hormone analogues such as FSH, LH and CG. For example, in one embodiment, the invention is to a method of performing a whole-blood TSH sandwich assay using at least two epitope-compatible antibodies comprising at least one capture antibody and at least one signal antibody. The Kd of both antibodies for TSH is less than or about 1 nM, e.g., no greater than 0.5 nM, no greater than 0.15 nM, or no greater than 0.1 nM. The capture antibody Kd values for FSH, LH and CG are greater than about 2500, greater than about 500 and greater than about 200 nM, respectively, and the signal antibody Kd values for FSH, LH and CG are greater than about 250, greater than about 200 and greater than about 35 nM, respectively. More preferably, the capture antibody Kd values for FSH, LH and CG are greater than about 1000, greater than about 1000 and greater than about 1000 nM respectively, and the signal antibody Kd value for LH is greater than about 35 nM. The method comprises the steps of:

(a) contacting a whole-blood sample with a TSH signal antibody and a TSH capture antibody immobilized on an electrochemical sensor to form a sandwich complex, and (b) detecting a signal associated with said complexed signal antibody.

The present invention has utility beyond detection of TSH. For example, in one aspect, the invention is to an analyte sandwich immunoassay performed in a whole-blood sample comprising at least two antibodies or other ligands comprising at least one capture antibody or ligand and at least one signal antibody or ligand, wherein the Kd for the analyte with said at least two antibodies or ligands is at least a preselected level lower, e.g., 500 times lower, 1000 times lower, or 10,000 times lower, than the Kd for at least two selected known cross-reactants (closely related by protein sequence contaminating antigens). In this aspect, the sandwich preferably is formed by substantially non-sequential antibody or ligand addition to the sample. The assay may be performed with a single wash step prior to detection. Here, for example, the target analyte can be one of TSH, FSH, LH and CG, and the cross-reactant may be selected from the group consisting of TSH, FSH, LH and CG but is not the target analyte. Thus, in other embodiments of the invention, the target analyte may be selected from one of FSH, LH and CG rather than TSH.

Low Wash Sandwich Immunoassays

The selective nature of the above-described antibodies or ligands for TSH over competing endocrine glycoprotein hormone analogues such as FSH, LH and CG lends the immunoassay, devices and methods of the invention particularly suitable for immunoassays that employ a limited wash step. Thus, the invention is particularly well-suited for implementation in point-of-care testing devices, such as the i-STAT® immunoassay platform, which may employ analytical test cartridges or devices that do not have sufficient space for a substantial amount of wash fluid.

With conventional TSH assays, employing multiple and repeated wash steps is critical for accurate results in order to ameliorate the cross-reactions involving one or more of FSH, LH and CG. According to some embodiments of the invention, the assay operates where the sandwich is formed by non-sequential antibody addition to a sample, i.e., capture and signal antibodies contact the sample roughly at the same time, and without an intervening wash step. The assay optionally includes a single wash step prior to detection, e.g., a single limited wash step that removes blood and unbound signal antibody from the capture antibody. Thus, in a second embodiment, the present invention relates to immunoassays having a reduced wash step. In one aspect of this embodiment, a single wash step is used to remove unbound analyte and signal antibodies from the sandwich assay.

In one aspect of this embodiment, the invention is to a TSH sandwich immunoassay, comprising at least two epitope-compatible antibodies comprising at least one capture antibody and at least one signal antibody, wherein the Kd of both antibodies for TSH is less than or about 1 nM, e.g., no greater than 0.5 nM, no greater than 0.15 nM, or no greater than 0.1 nM, and wherein the capture antibody Kd for FSH, LH and CG are greater than about 2500 nM, greater than about 500 nM and greater than about 200 nM, respectively, and wherein the immunoassay uses a single wash step. More preferably, the capture antibody Kd for FSH, LH and CG are greater than about 1000 nM, greater than about 1000 nM and greater than about 1000 nM, respectively. In this context, "a single wash step" refers to a wash step in which a wash fluid (which preferably is substantially free of analyte and signal antibodies) is directed to the immunosensor to remove unbound analyte and unbound signal antibodies from the region of the immunosensor. The amount of wash fluid employed in the single wash step may vary widely, but preferably is less than 1000 µL, less than 750 µL, less than 500 µL or less than 250 µL. The type of immunosensor employed in the present invention may vary widely and may be selected, for example, from an electrochemical sensor, a surface acoustic wave sensor, a surface plasmon resonance sensor, a thermal sensor, a field effect transistor sensor, an optical sensor, an evanescent wave sensor, a waveguide sensor and the like.

The invention is also directed to methods for detecting an analyte, e.g., TSH, with an immunoassay that employs no more than one washing step. For example, in one embodiment, the invention is to a method of performing a whole-blood TSH sandwich assay using at least two epitope-compatible antibodies comprising at least one capture antibody and at least one signal antibody. The Kd of both antibodies for TSH is less than or about 1 nM, e.g., no greater than 0.5 nM, no greater than 0.15 nM, or no greater than 0.1 nM. The capture antibody Kd values for FSH, LH and CG are greater than about 2500 nM, greater than about 500 nM and greater than about 200 nM, respectively, and the signal antibody Kd values for FSH, LH and CG are greater than about 250 nM, greater than about 200 nM and greater than about 35 nM, respectively. More preferably, the capture antibody Kd values for FSH, LH and CG are greater than about 1000 nM, greater than about 1000 nM and greater than about 1000 nM, respectively, and the signal antibody Kd value for LH is greater than about 35 nM. The method comprises the steps of: (a) contacting a whole-blood sample with a TSH signal antibody and a TSH capture antibody immobilized on an electrochemical sensor to form a sandwich complex, (b) washing sample and uncomplexed signal antibody from the sensor, and (c) detecting a signal associated with said complexed signal antibody.

In this embodiment, the washing fluid preferably comprises a fluid comprising water and one or more additives and should be capable of washing the sensors to the desired degree. In one aspect, the washing fluid comprises the enzymatic substrate ANPP (aminonitrophenyl phosphate). The washing fluid pH preferably is maintained to be optimal for the reporter enzyme, which, for alkaline phosphatase, is an optimal alkaline pH of from about 9 to 10. The washing fluid also preferably comprises a salt to affect electrical conductivity in an electrochemical assay which is supplied by sodium chloride and magnesium. The magnesium is also a cofactor of alkaline phosphatase, and may be present at low concentrations to enhance enzyme activity. Wash fluids for other enzyme based assays would also contain an appropriate enzymatic substrate, salts and buffers required for enzyme stability and, if electrochemical, for electrical conductivity in a solution, along with any appropriate enzyme cofactors.

Inclusion of Scavenger Beads for Known Interfering Substances

In a third embodiment, the invention is directed to a TSH sandwich immunoassay that employs one or more scavenger beads and to related devices and methods for conducting such immunoassays. To help enhance the selectivity of the assay for the analyte, e.g. TSH, an embodiment was devised where scavenger beads comprising for example latex or polystyrene beads labeled with an antibody to the cross-reactant, e.g. FSH, LH, CG, were added to the mixture that dissolves into the sample. Thus the cross-reactant is presented with comparatively unfavorable binding sites on the TSH capture antibody and comparatively favorable binding sites on beads dissolved into the sample.

In one aspect of this embodiment, for example, the invention is to an immunoassay comprising at least two epitope-compatible antibodies comprising at least one capture antibody and at least one signal antibody. The assay further comprises scavenger beads coated with antibodies (bead antibodies) to FSH, LH and CG, wherein the Kd for each of said antibodies is less than or about 1 nM, e.g., no greater than 0.5 nM, no greater than 0.15 nM, or no greater than 0.1 nM, for each of FSH, LH and CG, and the Kd of each of said bead antibodies for TSH is greater than about 250 nM. The Kd for TSH of the capture and signal antibodies employed in the immunoassay preferably is less than (or no greater than) about 1 nM, e.g., no greater than 0.5 nM, no greater than 0.15 nM, or no greater than 0.1 nM, as discussed above.

Thus, in one embodiment, the invention is to a TSH sandwich immunoassay with at least two epitope-compatible antibodies comprising at least one capture antibody and at least one signal antibody wherein one or more scavenger beads are used to reduce interference that otherwise may be caused by the competing endocrine glycoprotein hormone analogues FSH, LH and CG. Here, the Kd of the capture and signal antibodies for TSH is preferably less than or about 1 nM, e.g., no greater than 0.5 nM, no greater than 0.15 nM, or no greater than 0.1 nM. The added scavenger beads are coated with bead antibodies to FSH, LH and CG wherein the Kd for each of these antibodies is preferably less than or about 1 nM, e.g., no greater than 0.5 nM, no greater than 0.15 nM, or no greater than 0.1 nM, for each of FSH, LH and CG respectively.

In one aspect, the beads are coated with a single type of antibody that is selective for each of the competing endocrine glycoprotein hormone analogues. In another aspect, the beads are coated with multiple types of antibodies, wherein a first bead antibody is selective for FSH, a second bead antibody is selective for LH and a third bead antibody is selective for CG. Other combinations of bead antibodies may be possible, e.g., where a first bead antibody is selective for FSH and LH and a second bead antibody is selective for CG.

In another aspect, a plurality of different beads may be employed. For example, three different types of beads, each having a different antibody, may be employed to selectively bind to the competing endocrine glycoprotein hormone analogues. For example, the immunoassay, device and method may employ first beads, second beads and third beads to selectively bind to FSH, LH and CG, respectively. More specifically, the first beads may comprise a first bead antibody selective for FSH, the second beads may comprise a second bead antibody selective for LH and the third beads may comprise a third bead antibody selective for CG.

To avoid TSH preferentially binding to these beads, it is desirable that the Kd of each of the bead antibodies (whether on one type of bead or a plurality of types of beads) for TSH is greater than about 250 nM. Preparation of the scavenger beads in terms of antibody labeling follows the method described herein for the capture antibody for TSH. As with the embodiments described above, it is preferable that the TSH capture antibody Kd for FSH, LH and CG are greater than about 2500 nM, greater than about 500 nM and greater than about 200 nM, respectively. Likewise it is desirable that the TSH signal antibody Kd for FSH, LH and CG are greater than about 250 nM, greater than about 200 nM and greater than about 35 nM, respectively.

Note that the scavenger beads can be non-magnetic, and remain suspended in the sample and thus are removed to a waste chamber with the sample prior to the washing and detection steps. Alternatively, the scavenger beads may be magnetic and are drawn to a region of the device, by the application of a magnetic field, that is away from the TSH capture site region, e.g., the TSH immunosensor. Alternatively, the scavenger beads may be magnetic, but removed to a waste chamber with or without application of a magnetic field. Various means for magnetically retaining magnetic beads in immunosensors are described in U.S. Pat. Appl. No. 61/371,066 to Miller, the entirety of which is incorporated herein by reference.

The use of magnetic scavenger beads to reduce cross contaminant interference is illustrated in FIG. 8. As shown, magnetic beads that have scavenger antibodies selective for LH are added to the sample and selectively bind to LH contained in the sample. A magnetic field, e.g., from a permanent magnet or from an electromagnet, is applied either in the device (cartridge) or in the device reader so as to localize the magnetic beads in a region remote from and preferably upstream of the sensor. This advantageously results in reduced interference from the cross-reacting or competing analyte, here LH.

In a preferred embodiment, the sacrificial beads are incorporated into a dry reagent coating, which in some embodiments may be the same dry reagent coating that contains the signal antibody. Thus, in one embodiment, the analysis device includes a dry reagent coating that comprises either or both: (a) sacrificial beads suitable for ameliorating the effect of one or more of FSH, LH or CG, and/or (b) a signal-generating reagent such as a signal antibody or a labeled analyte. The dry reagent coating may be formed from a reagent cocktail, which also preferably comprises either or both: (a) sacrificial beads suitable for ameliorating the effect of one or more of FSH, LH or CG, and/or (b) a signal-generating reagent such as a signal antibody or a labeled analyte. In one aspect, the reagent coating and/or cocktail further comprises IgM or fragments thereof for ameliorating interference caused by heterophile antibodies, as disclosed in co-pending U.S. application Ser. No. 12/411,325, which is incorporated by reference in its entirety. The surface on which the reagent cocktail is to be deposited preferably is first Corona treated to provide charged surface groups that will promote spreading of the printed cocktail.

In general, the reagent cocktail used to form the dry reagent coating may further comprise a water-soluble protein, an amino acid, a polyether, a polymer containing hydroxyl groups, a sugar or carbohydrate, a salt and optionally a dye molecule. One or more of each component can be used. In one embodiment, the cocktail contains bovine serum albumin (BSA), glycine, salt, methoxypolyethylene glycol, sucrose and optionally bromophenol blue to provide color that aids visualizing the printing process. In one embodiment, from 1 to 20 µL of cocktail is printed onto the desired surface, e.g., within the holding chamber or other conduit, of the analysis device and allowed to air dry (with or without heating) before being assembled with its cover. In a preferred aspect, the reagent cocktail and the dry reagent coating formed therefrom comprise one or more of lactitol, DEAE-dextran, salts such as magnesium and sodium chloride, IgG/IgM, heparin, surfactant(s) and rhodamine.

The reagent cocktail preferably is formulated as a printable aqueous solution containing the sacrificial beads and optionally other interference-reducing reagents. Upon introduction of a biological sample, e.g., blood, the sample preferably mixes with the reagent in a first step of the assay. The reagent may also include inorganic salts and surfactants to optimize assay performance with respect to chemical and fluidic attributes. Other optional additives may include heparin to ensure adequate anticoagulation and dyes for visualization of the location of the reagent after printing. Also optionally present are stabilizers such as sodium azide for inhibition of microbial growth and a mixture of lactitol and diethylamino-ethyl-dextran (Applied Enzyme Technologies Ltd., Monmouth House, Mamhilad Park, Pontypool, NP40 HZ UK) for stabilization of proteins. Once deposited in the device, the deposited reagent may, for example, be dried for 30 to 60 minutes in a stream of warm air. In one embodiment, the reagent is printed in the sample inlet of the device using an automated printing instrument and dried to form a sacrificial bead containing reagent coating layer.

In another embodiment, the test cartridge may comprise a plurality of dry reagent coatings (in which case the coatings may be respectively referred to as a first reagent coating, a second reagent coating, etc., in order to distinguish them). For example, the sacrificial beads may be included in a first reagent coating, which, for example, may be adjacent to a second reagent coating that contains the signal antibody. In this aspect, the second reagent coating may be located upstream or downstream of the first reagent coating, although it is preferable for the reagent coating that contains the signal antibody to be located downstream of the reagent coating that contains the sacrificial beads. In a preferred embodiment, the holding chamber is coated with a first reagent coating that comprises sacrificial beads and optionally other reagents that ameliorate various forms of interference. In this aspect, a second reagent coating comprising the signal antibody preferably is located downstream of the holding chamber, e.g., immediately upstream of the immunosensor.

In still other embodiments, the sacrificial beads may not be part of the analysis device, e.g., cartridge. For example, the sacrificial beads may be incorporated in a sample collection device, e.g., capillary, Vacutainer™ or syringe. For example, the sacrificial bead coating may be formed on an interior wall of the collection device. Thus, in one embodiment, the invention is to a kit for performing an immunoassay that comprises the sacrificial beads which are first used to amend the blood sample in a first container or location, and then the sample is passed to a second container or location which has the capture and signal antibodies.

In addition or as an alternative to the beads discussed herein, the sample may be amended with sacrificial beads (optionally opsonized to leukocytes) of the type described in commonly owned U.S. application Ser. No. 12/620,179 to Campbell et al., the entirety of which is incorporated herein by reference.

Immunosensor Fabrication

As mentioned above, the present invention is best illustrated by reference to the i-STAT® system that uses electrochemical immunosensors. Wafer-level microfabrication of a preferred embodiment of the immunosensor is as follows. The base electrode consists of a square array of 7 µm gold disks on 15 µm centers. The array covers a circular region approximately 600 µm in diameter, and is achieved by photo-patterning a thin layer of polyimide of thickness 0.35 µm over a substrate made from a series of layers comprising $Si/SiO_2/TiW/Au$. The array of 7 µm microelectrodes afford high collection efficiency of electroactive species with a reduced contribution from any electrochemical background current associated with the capacitance of the exposed metal. The inclusion of a PVA layer, e.g., photoformable polyvinyl alcohol, over the metal significantly enhances the reduction of background currents.

The porous PVA layer preferably is prepared by spin-coating an aqueous mixture of PVA plus a stilbizonium photoactive, cross-linking agent over the microelectrodes on the wafer. The spin-coating mixture optionally includes bovine serum albumin (BSA). The PVA layer may then be photo-patterned to cover only the region above and around the arrays and preferably has a thickness of from about 0.2 to 1.0 µm, e.g., from 0.4 to 0.8 µm or about 0.6 µm. The immunosensor for different TSH antibodies may be made by coating the antibodies onto a bead and applying the beads to the sensor surface where they adhere.

Using the bead preparation method described below, a droplet of from about 30 to 60 mL, e.g., from 35 to 50 mL, or about 40 mL, comprising from about 0.6 to 2.0 wt %, e.g., from about 0.8 to 1.6 wt % or about 1 wt % solids in deionized water, may be microdispensed (using, for example, the method and apparatus of U.S. Pat. No. 5,554,339, incorporated here by reference) onto the photo-patterned porous polyvinyl alcohol permselective layer covering the sensor and allowed to dry. The dried particles should adhere to the porous layer substantially preventing their dissolution in the blood sample or the washing fluid.

Capture Bead Fabrication

The capture beads used for the present invention, whether used for the immobilized capture antibody or the optional scavenger bead antibody, may be formed by a variety of techniques. In a preferred embodiment, carboxylate-modified latex microparticles (Commercially available from Bangs Laboratories Inc. and Seradyn Microparticles Inc.) coated with anti-TSH and anti-HSA are both prepared by the same method. The particles preferably are first buffer exchanged by centrifugation, followed by addition of the antibody, which is allowed to passively adsorb onto the particles. The carboxyl groups on the particles are then preferably activated, e.g., with EDAC in IVIES buffer at pH 6.2, to form amide bonds to the antibodies. Any bead aggregates may be removed by centrifugation and the finished beads may be stored frozen, e.g., at about –80° C.

Cartridge Design

Figure 2:
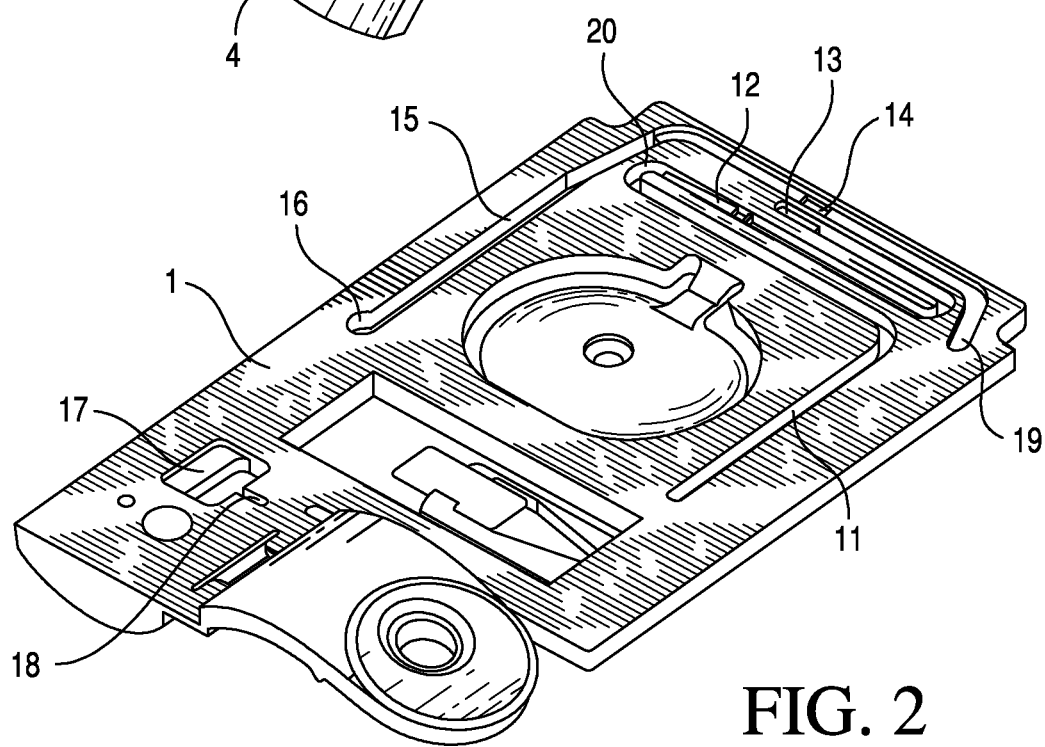
FIG. 2 is an isometric bottom view of an immunosensor cartridge cover.

Referring to the figures, an optional cartridge design for use in the present invention comprises a cover, FIGS. 1, 2, a base, FIG. 4, and a thin-film adhesive gasket, FIG. 3, disposed between the base and the cover. Referring now to FIG. 1, the cover 1 is made of a rigid material, preferably plastic, capable of repetitive deformation at flexible hinge regions 5, 9, 10 without cracking. The cover comprises a lid 2, attached to the main body of the cover by a flexible hinge 9. In operation, after introduction of a sample into the sample holding chamber 34, the lid can be secured over the entrance to the sample entry port 4, preventing sample leakage, and the lid is held in place by hook 3. The cover further comprises two paddles 6, 7, that are moveable relative to the body of the cover, and which are attached to it by flexible hinge regions 5, 10. In operation, when operated upon by a pump means, paddle 6 exerts a force upon an air bladder comprised of cavity 43, which is covered by thin-film gasket 21, to displace fluids within conduits of the cartridge. When operated by a second pump means, paddle 7 exerts a force upon the gasket 21, which can deform because of slits 22 and 23 cut therein. The cartridge is adapted for insertion into a reading apparatus, and therefore has a plurality of mechanical and electrical connections for this purpose. It should also be apparent that manual operation of the cartridge is possible. Thus, upon insertion of the cartridge into a reading apparatus, the gasket transmits pressure onto a fluid-containing foil pack filled with approximately 130 µL of analysis/wash solution ("fluid") located in cavity 42, rupturing the package upon spike 38, and expelling fluid into conduit 39, which is connected via a short transecting conduit in the base to the sensor conduit. The analysis fluid fills the front of the analysis conduit first pushing fluid onto a small opening in the tape gasket that acts as a capillary stop. Other motions of the analyzer mechanism applied to the cartridge may be used to inject one or more air segments into the analysis fluid at controlled positions within the analysis conduit. These segments are used to help wash the sensor surface and the surrounding conduit with a minimum of fluid.

The cover further comprises a hole covered by a thin pliable film 8. In operation, pressure exerted upon the film expels one or more air segments into a conduit 20 through a small hole 28 in the gasket.

Referring to FIG. 2, the lower surface of the base further comprises second conduit 11, and first conduit 15. Second conduit 11 includes a constriction 12, which controls fluid flow by providing resistance to the flow of a fluid. Optional coatings 13, 14 provide hydrophobic surfaces, which together with gasket holes 31, 32, control fluid flow between conduits 11, 15. A recess 17 in the base provides a pathway for air in conduit 34 to pass to conduit 34 through hole 27 in the gasket.

Referring to FIG. 3, thin-film gasket 21 comprises various holes and slits to facilitate transfer of fluid between conduits within the base and the cover, and to allow the gasket to deform under pressure where necessary. Thus, hole 24 permits fluid to flow from conduit 11 into waste chamber 44; hole 25 comprises a capillary stop between conduits 34 and 11; hole 26 permits air to flow between recess 18 and conduit 40; hole 27 provides for air movement between recess 17 and conduit 34; and hole 28 permits fluid to flow from conduit 19 to waste chamber 44 via optional closeable valve 41. Holes 30 and 33 permit the immunosensor chip (described above) that are housed within cutaways 35 and 37, respectively, to contact fluid within conduit 15. In a specific embodiment, cutaway 37 houses a ground electrode, and/or a counter-reference electrode, and cutaway 35 houses at least one analyte sensor and, optionally, a conductimetric sensor. Hole 29 permits the filter below access to an external air supply, permitting the generation of air bubbles streamed into the wash fluid flow. The edges of the air bubbles create distinct changes in the wash fluid effecting a partial washing over the sensors. Typical ELISA assays utilize distinct buffer changes (rather than partial washing) that permit effective washing of the capture sensors.

Referring to FIGS. 3 and 4, conduit 34 is the sample holding chamber that connects the sample entry port 4 to first conduit 11 in the assembled cartridge via opening 122 in gasket 21. Cutaway 35 houses the analyte sensor or sensors, or an analyte responsive surface, together with an optional conductimetric sensor or sensors. Cutaway 37 houses a ground electrode if needed as a return current path for an electrochemical sensor, and may also house an optional conductimetric sensor. Cutaway 36 provides a fluid path between gasket holes 31 and 32 so that fluid can pass between the first and second conduits. Recess 42 houses a fluid-containing package, e.g., a rupturable pouch, in the assembled cartridge that is pierced by spike 38 because of pressure exerted upon paddle 7 upon insertion into a reading apparatus. Fluid from the pierced package flows into the second conduit at 39. An air bladder is comprised of recess 43 which is sealed on its upper surface by gasket 21. The air bladder is one embodiment of a pump means, and is actuated by pressure applied to paddle 6 which displaces air in conduit 40 and thereby displaces the sample from sample chamber 34 into first conduit 15.

The location at which air enters the sample chamber (gasket hole 27) from the bladder, and the capillary stop 25, together define a predetermined volume of the sample chamber. In some preferred embodiments, the sample is metered to a sample volume of from 1 to 500 µL, e.g., from 5 to 200 µL, or from 10 to 50 µL, preferably about 20 µL. An amount of the sample corresponding to this volume is displaced into the first conduit when paddle 6 is depressed. This arrangement is therefore one possible embodiment of a metering means for delivering a metered amount of an unmetered sample into the conduits of the cartridge.

In the present cartridge, a means for metering a sample segment is provide in the base plastic part. The segment size is controlled by the size of the compartment in the base and the position of the capillary stop and air pipe holes in the tape gasket. This volume can be readily varied from 1 to 500 µL, e.g., from 1 to 200 µL. Expansion of this range of sample sizes is possible within the context of the present invention.

The fluid is pushed through a pre-analytical conduit 11 that can be used to amend a reagent (e.g., with one or more of scavenger beads, signal antibodies, or soluble molecules) into the sample prior to its presentation at the sensor conduit 19. Alternatively, one or more of the amending reagents may be located in one or more conduits. For example, the one or more reagents may be located in conduit 34 and/or conduit 15, beyond portion 16. Pushing the sample through the pre-analytical conduit also serves to introduce tension into the diaphragm pump paddle 7 which improves its responsiveness for actuation of fluid displacement.

In some assays, metering is advantageous if quantitation of the analyte is required. A waste chamber 44 is provided for sample and/or fluid that is expelled from the conduit, to prevent contamination of the outside surfaces of the cartridge. A vent 45 connecting the waste chamber to the external atmosphere is also provided. A feature of the cartridge is that once a sample is loaded, analysis can be completed and the cartridge discarded without the operator or others contacting the sample.

Figure 5:
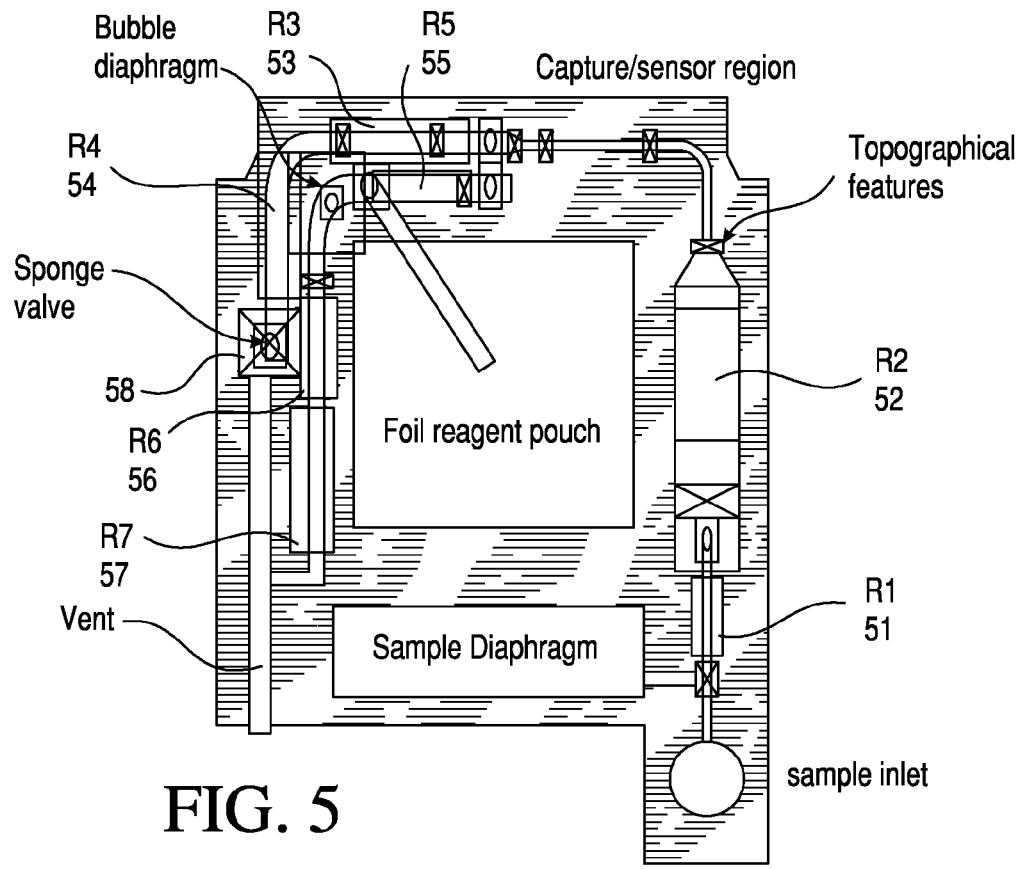
FIG. 5 is a schematic view of the layout of an immunosensor cartridge.

Referring now to FIG. 5, a schematic diagram of the features of a cartridge and components is provided, wherein 51-57 are portions of the conduits and sample chamber that can optionally be coated with dry reagents to amend a sample or fluid. The sample or fluid is passed at least once over the dry reagent to dissolve it. Reagents used to amend samples or fluid within the cartridge may include antibody-enzyme conjugates, signal antibodies, blocking agents that prevent either specific or non-specific binding reactions among assay compounds, or sacrificial beads (discussed above). A surface coating that is not soluble but helps prevent non-specific adsorption of assay components to the inner surfaces of the cartridges can also be provided.

Within a segment of sample or fluid, an amending substance can be preferentially dissolved and concentrated within a predetermined region of the segment. This is achieved through control of the position and movement of the segment. Thus, for example, if only a portion of a segment, such as the leading edge, is reciprocated over the amended substance, then a high local concentration of the substance can be achieved close to the leading edge. Alternatively, if a homogenous distribution of the substance is desired, for example, if a known concentration of an amending substance is required for a quantitative analysis, then further reciprocation of the sample or fluid will result in mixing and an even distribution.

In specific embodiments, a closeable valve 58 is provided between the first conduit and the waste chamber. In one embodiment, valve 58 is comprised of a dried sponge material that is coated with an impermeable substance. In operation, contacting the sponge material with the sample or a fluid results in swelling of the sponge to fill the cavity 41, thereby substantially blocking further flow of liquid into the waste chamber 44. Furthermore, the wetted valve also blocks the flow of air between the first conduit and the waste chamber, which permits the first pump means connected to the sample chamber to displace fluid within the second conduit, and to displace fluid from the second conduit into the first conduit in the following manner. After the sample is exposed to the sensor for a controlled time, the sample is moved into the post-analytical conduit 19 where it can be amended with another reagent. It can then be moved back to the sensor and a second reaction period can begin. Alternately, the post-analysis conduit can serve simply to separate the sample segment from the sensor.

Figure 6:
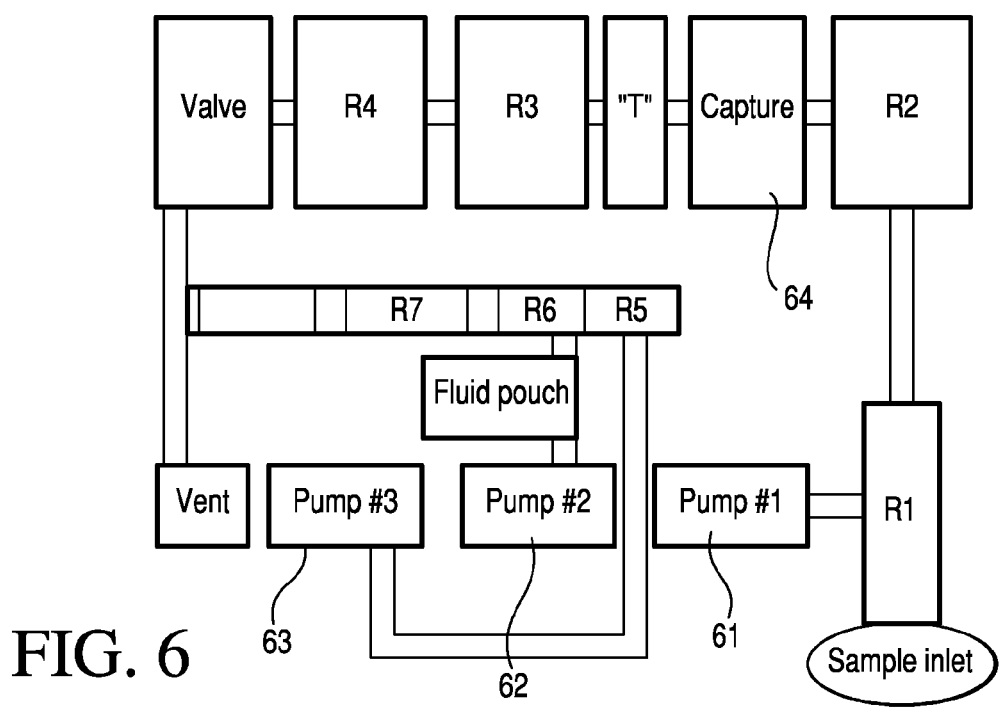
FIG. 6 is a schematic view of the fluid and air paths within an immunosensor cartridge, including sites for amending fluids with dry reagents.

FIG. 6 illustrates the schematic layout of an immunosensor cartridge comprising three pump means, 61-63. While these pumps have been described in terms of specific embodiments, it will be readily understood that any pump means capable of performing the respective functions of pump means 61-63 may be used within the present invention. Thus, pump means 1, 61, must be capable of displacing the sample from the sample holding chamber into the first conduit; pump means 2, 62, must be capable of displacing fluid within the second conduit; and pump means 3, 63, must be capable of inserting at least one segment into the second conduit.

Operation

In a preferred embodiment, in a first step, the user draws a blood sample from the patient (or as in the cases below uses a control fluid with a known TSH concentration) and inserts a few drops into the cartridge. Once the cartridge is inserted into the instrument, the instrument controls the rest of the test cycle. The signal antibody preferably is coated on the wall of a conduit (e.g., holding chamber) in the cartridge, dissolves into the sample and a portion of the sample is moved by the pump to the location of the immunosensor. Alternatively, the signal antibody may be disposed in a coating of a conduit in the region of the immunosensor or elsewhere in the device, but ideally in a location upstream of the immunosensor. The pump also oscillates the sample to help promote sandwich formation on the sensor. This may take from about 1 to 20 minutes, preferably from 2 to 14 minutes, from 4 to 12 minutes, or ideally about 8 minutes. Then the pump forces the sample into a waste chamber. For embodiments that include a separate wash step, wash fluid from the internal liquid pouch may be delivered via a pump over the immunosensor to wash away any residual sample and unbound signal antibody. A portion of the fluid, which also contains the enzyme substrate, remains in the region of the sensor. Measurement of the current at the immunosensor is then made. Software within the instrument records the values, e.g., currents and other data as shown in the tables in the examples section, or calculates and displays an actual analyte concentration.

In operation of the preferred embodiment, which is an amperometric electrochemical system, the currents associated with oxidation of p-aminophenol at the immunosensor arising from the activity of ALP, are recorded by the analyzer. The biochemistry of ALP dephosphorylation of various phosphorylated substrates is well known. The potential at the immunosensor is poised with respect to a silver-silver chloride reference electrode.

Many types of immunoassay devices and processes have been described and the following jointly owned patents and applications. A disposable sensing device for successfully measuring analytes in a sample of blood is disclosed by Lauks in U.S. Pat. No. 5,096,669. It employs a reading apparatus and a cartridge that fits into the reading apparatus for the purpose of measuring analyte concentrations in a sample of blood. U.S. Pat. No. 7,723,099 to Miller et al. describes an immunoassay device with an immuno-reference electrode; U.S. Pat. No. 7,682,833 to Miller et al. describes an immunoassay device with improved sample closure; U.S. Pat. Appl. Pub. 2004/0018577 to Campbell et al. describes a multiple hybrid immunoassay; U.S. Pat. No. 7,419,821 to Davis et al. describes an apparatus and methods for analyte measurement and immunoassay; and U.S. Pat. Appl. Pub. 2010/0167301 to Collier et al. describes immunoassay compositions and methods using nucleotide conjugates. Each of these patents and applications is incorporated herein by reference in its entirety.

It is well known in the art that immunoassays are susceptible to various forms of interferences. Jointly-owned pending U.S. application Ser. No. 12/411,325 (the "'325 Application"), for example, addresses ameliorating interferences from heterophile antibodies by the inclusion of IgM into an IgG reagent cocktail. The '325 application is incorporated herein by reference in its entirety.

Empirical Versus Theoretical Approaches to Antibody Selection for Low Wash TSH Assays For a TSH assay, the related hormones can potentially be found at high molar concentrations compared to TSH in a number of clinical situations. Therefore, FSH, LH and CG are typically added to a TSH assay at the levels of 500, 500, and 200,000 mIU/mL, respectively, to simulate a real sample in the presence of high concentrations of cross-reacting species (Architect Product Data Insert, Abbott, Chicago, Ill.). These concentrations for TSH, FSH, LH and CG are approximately 0.96, 3000, 760 and 436,000 pM, respectively.

Theoretical Cross Reactivity

Once the equilibrium dissociation constants have been measured, theoretical calculations can be performed in order to compare anticipated cross reactivity based on the obtained dissociation constants. These calculations cannot exactly predict the outcome of the actual assay, but may be used as a guide to ensure that the affinity of the antibodies will suffice for performing the assay, and that selected antibodies will perform significantly better when tested in low wash cartridge experiments. These calculations can also aid development of the assay by identifying unexpected assay results during the prototype phase of development. See, e.g., Table 1, below.

Calculations were performed by assuming a two-step assay and prior to a wash procedure, the two-step assay comprising: (1) a capture step and (2) a detection step. In the capture step it is assumed that all four hormones bind with the capture antibody and reach equilibrium. The concentration of each hormone bound to the capture antibody after this step is considered the captured hormone. In the detection step, the captured hormone is assumed to reach equilibrium in binding to the detection antibody. The concentration of each hormone bound to the detection antibody after this second step is the detected concentration. The cross reactivity is then calculated by dividing the detected concentration of the interfering hormone by the detected concentration of TSH and multiplying by 100%. The measured dissociation constants for the antibodies given in Table 8 were used for the calculations. The concentrations for TSH, FSH, LH and CG are approximately 1, 3000, 760 and 436,000 pM, respectively. These values are comparable to those typically added to a TSH assay in order to challenge the assay. This calculation is used to confirm that the antibodies selected are an improvement over the control antibodies. The calculation assumes 100 pM capture antibody and 100 pM detection antibody.

Since the model cannot exactly predict the outcome in an actual assay as other factors such as determining a compatible antibody pair or the impact of mass transport for the capture antibody, the data is simply used as a guide to confirm that the antibodies have merit, and estimate target dissociation constants. Therefore, in order to compare the antibodies, the values determined from the cross reactivity calculation are compared in the following manner. The control cross reactivity values are defined by performing the above calculation using antibodies TSH Ab 544 and 414B. The best value for cross reactivity obtained for these control antibodies is taken to be the cross-reactivity which must be improved upon. This value is indicated with an asterisk for each hormone in Table 1, below. Any candidate antibody pair should have lower cross-reactivity than these values in both configurations. From the data in the table, we see that the combination of 414B and 5409 has a condition in which the cross reactivity to FSH and CG are above the control values. This result suggests that this combination may not be the best pair for a TSH assay. The table also indicates that combinations of 5409, ME130 and T25C yield values of cross reactivity below the control values in either combination, for all hormones. This indicates that these antibodies may be good candidates for use in the assay and were investigated further.

TABLE 1

CROSS-REACTIVITY PERCENT - CALCULATED

| Capture Ab | Signal Ab | FSH | LH | CG |
|---|---|---|---|---|
| 5409 | ME130 | 0.04 | 0.01 | 40 |
| ME130 | 5409 | 0.04 | 0.01 | 7.3 |
| 5409 | T25C | 0.02 | 0.01 | 75 |
| T25C | 5409 | 0.02 | 0.01 | 12 |
| 414B | 5409 | 0.73 | 0.03 | 6 |
| 5409 | 414B | 11 | 0.03 | 7800 |
| Control | | | | |
| TSH Ab 544 | 414B | 145 | 0.74* | 85,200 |
| 414B | TSH Ab 544 | 10* | 0.79 | 120* |

*Denotes poor sandwich antibody pairs.

The present invention will be better understood in view of the following non-limiting examples.

Example 1

Initial Antibody Screening

Sixty-seven antibody preparations were obtained (Table 2) and tested with a nitrocellulose dot blot assay. Additionally, TSH Antibody 544 and Seradyn anti-alpha-LH monoclonal antibody (Seradyn, Cat#MIT0414B) were used in these studies as benchmark cross-reacting pair of antibodies. To provide assay standards, the antigens TSH (Cat#T9265, Sigma, St. Louis, Mo.), FSH (Cat#F4021, Sigma, St. Louis, Mo.), LH (Cat#L5259, Sigma, St. Louis, Mo.) and CG (Cat#C0434, Sigma, St. Louis, Mo.) were resuspended in ⅓ PBS buffer to an approximate concentration of 35,000 uIU/mL, 700,000 mIU/mL, 250,000 mIU/mL, $2\times10^7$ mIU/mL, for TSH, FSH, LH, and CG, respectively. One μL of each antigen was spotted and dried onto a small strip of nitrocellulose. The nitrocellulose strip was first blocked with 1% powdered milk in PBS, then individual strips were incubated with each of the different antibody preparations. The strips were then washed with PBS, 0.05% Tween-20, followed by addition of Goat anti-mouse IgG H+L ALP secondary conjugate (Cat#4751-1806, Kirkegaard & Perry, Gaithersburg, Md., USA) and where appropriate anti-rabbit, sheep, and goat IgG H+L ALP conjugates were used for certain polyclonals, then the BCIP/NBT alkaline phosphatase substrate (1-component) (Cat#50-81-07, Kirkegaard & Perry, Gaithersburg, Md., USA) was added. The reaction was stopped by rinsing in deionized water.

TABLE 2

LIST OF SCREENED ANTIBODIES

| Vendor | Catalogue # |
|---|---|
| Immunoreagents | MuxHu-012A-Q |
| | MuxHu-012B-Q |
| | MuxHu-012C-C |
| | GtxHu-012-D |
| Maine Biotechnology Services | MAB128P |
| | MAB129P |
| | MAB130P |
| | MAB131P |
| | MAB132P |
| Biospacific | 5405 |
| | 5409 |
| | G-109-C |
| | S-109-C |
| | 5401 |
| | 5403 |
| | 5404 |
| Hytest | Anti-h TSH 11E4 |
| | Anti-h TSH 7G12 |
| | Anti-h TSH 10C7 |
| | Anti-h TSH 5E8 |
| | Anti-h TSH TSB1 |
| | Anti-h TSH TSB4 |
| Santa Cruz Biotech | sc-7813 |
| | sc-7814 |
| | sc-7815 |
| | sc-28917 |
| Seradyn | M1T0401 |
| | M1T0406 |
| | M1T0409 |
| | M1T0412 |
| | M1T0414 |
| Meridian Life Sciences | MAT04-004 clone 057-11004 |
| | MAT04-410 clone 204-12410 |
| | MAT04-176 clone 090-11176 |
| | MAT04-127 clone 090-10127 |
| | MDT04-005 clone 057-11005 |
| | MAT04-005 clone 057-11005 |
| | MAT04-252 clone 204-12252 |
| | MAT04-006 clone 057-11006 |
| | MAT04-003 clone 057-11003 |
| | MCT04-001 clone 057-11001 |
| ThermoScientific Pierce | MA1-82908 |
| | MA1-82909 |
| | MA1-83492 |
| Immunoreagents | GtxHu-012-D |
| | ShxHu-012-D |
| Biospacific | G-109-C |
| | S-109-C |
| Abd Serotec | 8920-0456 |
| | 8920-0600 |
| | 8920-0609 |
| | 0200-0064 clone 154 |
| | 0200-0065 clone 155 |
| | 8926-0511 |
| Meridian Life Sciences | D92409G |
| Chromaprobe | UHS115 |
| AbCam | ab9390 ME-130 |
| | ab1989 ME-128 |
| | ab9239 ME-131 |
| Fitzgerald | 10C-CR2151M3 |
| | 10C-CR2151M4 |
| | 10C-CR2151M5 |
| | 10C-CR2151M6 |
| | 10-T25D |
| | 10-T25A |
| | 10R-T128A |
| | 10-T15A |
| | 10-T15B |
| | 10-T15C |
| | 10-T25B |
| | 10-T25C |

Antibodies selected for further evaluation were determined by identifying those strips exhibiting good signal with the TSH antigen, and low signal with FSH, LH, and CG. This resulted in twenty-five candidate antibodies for further evaluation (Table 3), including TSH Ab 544 and Seradyn MIT0414B as controls.

TABLE 3

CANDIDATE ANTIBODIES FOR FURTHER CROSS-REACTIVITY ANALYSIS

| Vendor | ID |
| --- | --- |
| Abbott Diagnostics Division | TSH Ab 544 |
| Seradyn (Thermo-Fisher) | MIT0414B |
| Hytest | 5E8 |
| Hytest | 7G12 |
| Abd Serotec | 8920-0600 |
| Abd Serotec | 0200-0064 |
| Meridian Life Sciences | MAT04-127 |
| Meridian Life Sciences | MAT04-252 |
| Abcam | ME-128 |
| Thermoscientific Pierce | MA1-82908 |
| Abcam | ME-130 |
| Abcam | ME-131 |
| Biospacific | 5404 |
| Biospacific | 5409 |
| Fitzgerald | 10-T25B |

TABLE 3-continued

CANDIDATE ANTIBODIES FOR FURTHER CROSS-REACTIVITY ANALYSIS

| Vendor | ID |
| --- | --- |
| Fitzgerald | 10-T25C |
| Fitzgerald | 10C-CR2151M3 |
| Fitzgerald | 10C-CR2151M4 |
| Fitzgerald | 10-T25D |
| Fitzgerald | 10-T25A |
| Fitzgerald | 10R-T128A |
| Fitzgerald | 10-T15A |
| Fitzgerald | 10-T15C |
| Fitzgerald | 10C-CR2151M5 |
| Fitzgerald | 10-T15B |

The twenty-five candidate antibodies were then used to generate both capture beads and ALP conjugates as described in Examples 10 and 11, below. These reagents were built into i-STAT® cartridges and then screened for cross-reactivity using the test cycle described herein. The concentrations of the antigens (control test fluids) were approximately 0.4 mIU/L, 500 mIU/L, 500 mIU/L, and 200,000 mIU/L for TSH (ThermoFisher, Cat#ABT0315), FSH, LH and CG, respectively. FSH, LH and CG reagents were from the same source as described above. The assays were performed with TSH alone, as well as with TSH in combination with each CG, FSH, and LH individually. The percent cross reactivity was calculated by the difference between the electrochemical signal generated from TSH with one of the cross reacting antigens, less the TSH signal by itself divided by the signal generated by TSH alone.

This screening led to four candidate antibodies used for additional evaluation (Table 4). The TSH Ab 544 and MIT0414B antibodies were used for comparison studies, as high cross reacting controls. Vendor supplied data from the antibodies with the lowest relative cross reactivity are listed in Table 4. It should be noted that these had the lowest levels of cross reactivity with the antigen samples used. It was later identified and confirmed by testing these interfering antigens using the Abbott Architect i2000SR instrument (Chicago, Ill., USA) that these antigens contained trace amounts of TSH antigen, leading to an observed higher level of cross reactivity which was not seen in later experiments as higher purity antigens were used (purchased from Fitzgerald, North Acton, Mass.). As the cross reactivity levels were lower relative to the other antibodies tested, these antibodies were anticipated to have the best cross reacting performance and were further analyzed by other techniques described below.

TABLE 4

VENDOR INFORMATION FOR SELECTED ANTIBODIES

| Company | Cat# | Species | Type | Clone | Immunogen | Epitope | Ka (L/mol) |
| --- | --- | --- | --- | --- | --- | --- | --- |
| AbCAM | ME-130 (ME130) | Mus | mAb IgG1 | Ab9390 | Full length human TSH | Beta-TSH | $2 \times 10^{10}$ |
| Fitzgerald | 10C-CR2151M4 (M4) | Mus | mAb IgG1 | 157155 | Human Pituitary TSH | TSH | $2 \times 10^{10}$ |
| Fitzgerald | 10-T25C (T25C) | Mus | mAb IgG1 | M94206 | Human Pituitary TSH | Beta-TSH | $2 \times 10^{10}$ |
| Biospacific | 5409 SPTNE-5 (5409) | Mus | mAb IgG1 | N/A | N/A | TSH | $9.3 \times 10^{8}$ |

Example 2

FRET Epitope Mapping

Antibody Pair Compatibility was determined by Forster Resonance Energy Transfer (FRET) based competition assays. Approximately 500 to 1000 µg of each endocrine glycoprotein hormone (TSH (Cat#T9265, Sigma, St. Louis, Mo.), FSH (Cat#30R-AF020, Fitzgerald, North Acton, Mass.), LH (Cat#30-AL15, Fitzgerald, North Acton, Mass.), and CG (Cat#30R-AC048, Fitzgerald, North Acton, Mass.) were labeled with Alexa-Fluor® 488 Carboxylic Acid succinimidyl ester (Cat#A20100, Invitrogen, Carlsbad, Calif.). The antibodies were labeled with BHQ-10 Carboxylic Acid succinimidyl ester (Cat#BHQ-10S, Biosearch Technologies, Inc., Novato, Calif.) as a fluorescent quenching moiety. The proteins were labeled according to Ruan et al. (2009, Analytical Biochemistry, vol 393:196).

The antibody pairs were selected based on their quenching capability in the presence of an unlabeled antibody. Excess amount of the six antibodies was first incubated with the fluorescently labeled antigen, and then each sample was divided into six test tubes. In the six test tubes, one of the six BHQ labeled antibodies was added. Thus, a 6×6 reaction matrix was generated as shown in Table 5. The fluorescence intensity from each test tube was measured before and after the addition of the BHQ-labeled antibody. Significant change in fluorescence intensity indicated positive sandwich pairing. No change or little change in fluorescence intensity indicated the presence of the unlabeled antibody blocking the binding of the BHQ labeled antibody to the same analyte. Fluorescence was normalized to a value of 1.0 for same pairs. Table 5 provides relative fluorescence values.

TABLE 5

|  |  | BHQ labeled antibodies |  |  |  |  |
|---|---|---|---|---|---|---|
|  |  | 5409 | T25C | ME130 | M4 | TSH Ab 544 | 414B |
| Unlabelled Antibodies | 5409 | 1* | 0.78 | 0.78 | 0.90* | 0.93* | 0.88* |
|  | T25C | 0.95* | 1* | 0.97* | 0.92* | 0.97* | 0.97* |
|  | ME130 | 0.82 | 0.88* | 1* | 0.77 | 0.82* | 0.99* |
|  | M4 | 0.94* | 0.74 | 0.76 | 1* | 0.98* | 0.90* |
|  | TSH Ab 544 | 0.96* | 0.71 | 0.72 | 0.92* | 1* | 0.89* |
|  | 414B | 0.81 | 0.76 | 0.86* | 0.75 | 0.83* | 1* |

*Denotes poor sandwich antibody pairs.

Example 3

Epitope Mapping with i-STAT® Cartridge

Both polystyrene beads and ALP conjugates were generated for each of the six antibodies (described in Example 2). The cartridges were tested with 0.4 mIU/L TSH (recombinant TSH, ThermoFisher, Cat#ABT0315, Fremont, Calif., USA) generating an electrochemical current (nA). Table 6 lists a number of antibody pairs which indicate compatible antibody pairs. Same antibody pair combinations were not tested. For example, 414B recognizes the alpha subunit which would be anticipated to have high cross reactivity due to the biology of the binding and was not tested in the cartridge. It should be appreciated that there is a potential for epitope blocking by labeling the antibody with either fluorescent tags or fluorescent quenching moieties, which could account for the difference between both the FRET and sandwich ELISA methods, particularly for T25C with BHQ labeled 5409 and M4. Antibody pairs were tested in the electrochemical immunoassay system of the i-STAT cartridge using TSH antigen at 30 mIU/L concentration. Values in Table 6 are in nA of current measured.

TABLE 6

|  |  | Detection Conjugate Antibody |  |  |  |  |  |
|---|---|---|---|---|---|---|---|
|  |  | 5409 | T25C | ME130 | M4 | TSH Ab 544 | 414B |
| Capture Antibody | 5409 | NT* | 34.59 | 53.64 | 15.19* | 1.41* | NT* |
|  | T25C | 49.71 | NT* | 0.68* | 40.90 | 0.83* | 0.82* |
|  | ME130 | 54.66 | −0.10* | NT* | 50.53 | 10.76* | NT* |
|  | M4 | 20.67* | 22.52 | 39.92 | NT* | 0.00* | NT* |
|  | TSH Ab 544 | 7.98* | 22.43 | 34.85 | 0.11* | NT* | 25.0 |
|  | 414B | 40.29 | NT* | NT* | 41.27 | 10.15* | NT* |

*Denotes poor antibody pairs.
NT = Not tested

Antibody pairs for cross reactivity evaluation are listed in Table 7 based on the FRET competition assay and i-STAT® cartridge data.

TABLE 7

POSSIBLE ANTIBODY PAIRS FOR FURTHER EVALUATION

| Capture | Signal |
|---|---|
| 5409 | T25C |
| 5409 | ME130 |
| T25C | 5409 |
| T25C | M4 |
| ME130 | 5409 |
| ME130 | M4 |
| M4 | T25C |
| M4 | ME130 |
| TSH Ab 544 | T25C |
| TSH Ab 544 | ME130 |
| TSH Ab 544 | 414B |
| 414B | 5409 |
| 414B | M4 |

Example 4

Kd Calculations

Approximately 500 to 1000 μg of each endocrine glycoprotein hormone (TSH (Cat#T9265, Sigma, St. Louis, Mo.), FSH (Cat#30R-AF020, Fitzgerald, North Acton, Mass.), LH (Cat#30-AL15, Fitzgerald, North Acton, Mass.), and CG (Cat#30R-AC048, Fitzgerald, North Acton, Mass.) were labeled with Alexa-Fluor® 488 Carboxylic Acid succinimidyl ester (Cat#A20100, Invitrogen, Carlsbad, Calif.). The antigen was also labeled with BHQ-10 Carboxylic Acid succinimidyl ester (Cat#BHQ-10S, Biosearch Technologies, Inc., Novato, Calif.) as a fluorescent quenching moiety. The proteins were labeled according to Ruan et al. (2009, Analytical Biochemistry, vol 393:196).

Figure 7:
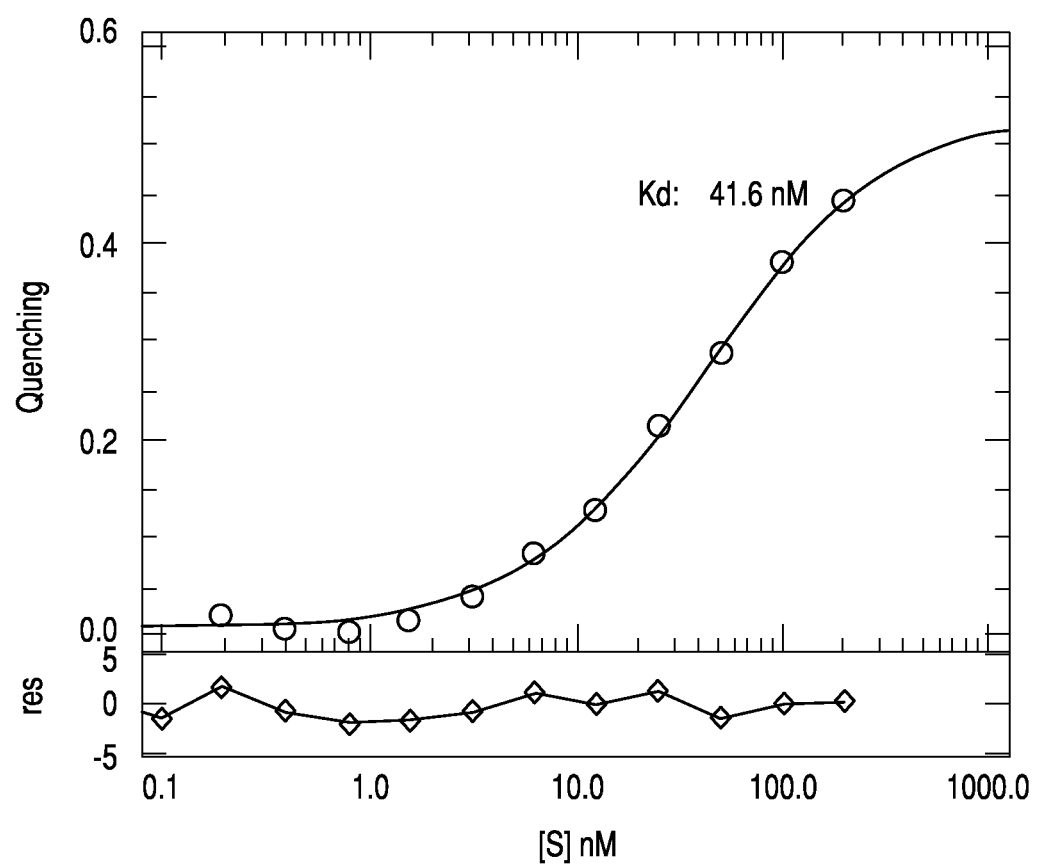
FIG. 7 shows FRET based binding data for CG and determination of its Kd value.

The addition of approximately 100 to 250 nM concentration of BHQ conjugated antibody with from 100 pmol for TSH to about 1000 pmol for LH, CG and FSH of each of the Alexa-Fluor® 488 labeled antigens was performed using an SLM-Aminco Model SLM 8100 spectrofluorometer according to Ruan et al, (2009, Analytical Biochemistry, vol 393: 196). The data was analyzed with IDL software (ITT, Boulder, Colo.) to generate a Kd value (nM). An example of the data is seen in FIG. 7. A summary of the Kd data is found in Table 8. ME130, M4 and 414B did not have the antibody characteristics of Tables 9 and 11 and therefore do not exhibit the low level of cross reactivity. Table 8 provides Kd binding data for six antibodies using 4 different antigens; all values are in nM.

TABLE 8

| Antibody | TSH | FSH | LH | CG |
|---|---|---|---|---|
| 5409 | 0.1 | 1000 | 1000 | 500 |
| T25C | 0.08 | 300 | 35 | 40 |
| ME130 | 0.04 | 70 | 54 | 45 |
| M4 | 0.18 | 210 | 300 | 554 |
| TSH Ab 544 | 1.31 | 1000 | 1000 | 210 |
| 414B | 0.04 | 0.1 | 0.05 | 0.05 |

It is important that the antibody generate sufficient signal as the cross reactivity levels are higher for low signal. Therefore, antibodies without sufficiently low Kd values (high affinity for TSH) in Table 9 were not considered for cross-reactivity. This generated the new list of possible antibody pairs for cross reactivity testing (Table 10).

TABLE 9

PREFERRED ANTIBODY TSH BINDING CHARACTERISTICS
TO GENERATE LOW CROSS REACTIVITY

|  | Kd TSH (nM) |
|---|---|
| Capture/Signal Antibody | ≤0.15 |

TABLE 10

REMAINING POSSIBLE ANTIBODY PAIRS
WITH ADEQUATE TSH ANTIGEN AFFINITY

| Capture | Signal |
|---|---|
| 5409 | T25C |
| 5409 | ME130 |
| T25C | 5409 |
| ME130 | 5409 |
| 414B | 5409 |

Those antibodies having the antibody Kd characteristics found in Table 11 were anticipated to have low cross-reactivity.

TABLE 11

PREFERRED ANTIBODY CHARACTERISTICS
TO GENERATE LOW CROSS REACTIVITY

|  | Kd FSH (nM) | Kd LH (nM) | Kd CG (nM) |
|---|---|---|---|
| Capture Antibody | >1000 | >1000 | >500 |
| Signal Antibody | >250 | >35 | >35 |

Example 5 i-STAT® Cross-Reactivity Data

Conjugated antibody bead preparations and Alkaline Phosphatase (ALP) conjugate combinations were built into i-STAT® immunoassay cartridges.

Based on compatible antibody pairs (Table 7), appropriate Kd values for TSH (Table 9), and high Kd values for FSH, LH and CG (Table 11), the combinations of Table 10 were tested for cross reactivity as described in Example 1, and are summarized in Table 12. Antibody pairs exhibiting cross reactivity greater than 5% for any of the interfering antigens were indicated with an asterisk (*). Only 5409 (capture antibody) and T25C (signal antibody) exhibited cross reactivity of less than 5% as they are the only antibodies with the characteristics described in Tables 9 and 11.

The antibody combination of 5409 used as a capture with T25C used as a detection antibody were the only pair capable of conferring low cross-reactivity due to their antigen binding characteristics, along with their ability to recognize compatible epitopes. ME130 had better binding affinity to TSH, which was exhibited with higher amperometric current generation. Antibodies exhibiting higher amperometric signals generated lower cross reactivity compared to those antibody pairs generating lower amperometric signals, which were more problematic to differentiate from the noise in the system. Table 12 indicates antigen cross reactivity in the i-STAT® cartridge format using 0.4 mIU/L TSH and adding all of the antigen concentrations. Only compatible antibody pairs determined previously were selected. M4 was removed from the selection as it had poor affinity to TSH, and generated low signal in the cartridge assay compared to other antibody combinations (Table 6 and Table 8).

TABLE 12

| Capture Ab | Detection Ab | FSH CR (%) | LH CR (%) | CG CR (%) |
|---|---|---|---|---|
| 5409 | ME130* | 2.43* | 10.08* | 0.78* |
| 5409 | T25C | 0.65 | 3.76 | 0.96 |
| T25C | 5409* | 6.25* | 9.89* | 13.72* |
| ME130 | 5409* | 3.90* | 11.05* | 11.84* |
| 414B | 5409* | 260.5* | 347.64* | 84.6* |
| Control |  |  |  |  |
| 414B | TSH Ab 544* | 219.21* | 467.21* | 39.17* |
| 94544 | 414B* | 7.15* | 11.75* | 117.14* |

*Denotes pairs with less desirable cross-reactivity above 5%.

Example 6

Anti-FSH 95784 Bead Preparation

The Anti-FSH 95784 beads were prepared as follows: 15 mg of 1.01 μm carboxylated polystyrene microparticles (10% weight/volume) (part#PCO4N, Bangs Laboratories Inc., USA), were reacted with 1.2 mg of Anti-FSH 95784 in 25 mM 2-(N-morpholino) ethanesulfonic acid (IVIES buffer, pH 6.2) for 15 minutes, and then were centrifuged to remove the supernatant. After resuspension of the pellet in 25 mM IVIES buffer, 10 mM carbodiimide (EDAC) was added to the sample and reacted for 2 hours at 4° C. This was followed by centrifuging the sample, washing the pellet with ⅕ physiological phosphate buffer twice. A formulated sample with 10% solids in phosphate buffer including 0.05% Tween 20 was stored for further use.

These beads were used in the assembly of FSH detecting cartridges where the TSH capture antibody is replaced with FSH conjugated beads. The beads were formulated to 3.2% solids in ⅕ physiological phosphate buffer, including 25% protein stabilization solution (Cat#Q2030529P1, Gwent Group, Pontypool, United Kingdom). A formulation of 0.8% solid, 0.8% protein stabilization in 0.08% Tween-20 was printed on chips and built into FSH cartridges.

Approximately 5 to 10 mg/mL (or 0.5 to 1% solid) of FSH beads were spiked into the test sample containing approximately 500 mIU/mL FSH, mixed vertically with pipette and immediately injected into the sample inlet of the FSH detecting cartridge. The beads can also be printed onto the sample inlet of the cartridge and dissolved into the sample later as the sample is introduced into the cartridge.

Example 7

LH Bead Preparation

LH polystyrene beads were prepared similar to Example 6, above, except that Biospacific LH 5304 antibody was used in place of Anti-FSH 95784. And as in Example 6, above, these beads were used to make LH detecting cartridges.

Example 8

FSH Magnetic Bead Preparation

FSH magnetic beads were prepared as follows: 15 mg of 0.70 μm super paramagnetic microsphere (10% weight/volume) (Catalog #MC04, Bangs Laboratories Inc, USA) were reacted with 30 mM carbodiimide (EDAC) in 50 mM 2-(N- morpholino) ethanesulfonic acid (IVIES buffer, pH 6.2) in a centrifuge tube for 15 minutes. The tube was placed on a magnet to attract the magnetic beads to the side of the magnet while aspirating out the supernatant. After two washes with 50 mM IVIES, 1.2 mg of Anti-FSH 95784 (Abbott Diagnostics Division) was reacted with the beads for 90 minutes at 4° C. The beads were separated from the supernatant by placing a magnet to the side of the centrifuge tube, and then remove the supernatant. This was followed by washing the pellets with ⅕ physiological phosphate buffer twice. A formulated sample with 5% solids in phosphate buffer including 0.05% Tween 20 was stored for further use.

Approximately 5 to 10 mg/mL (or 0.5 to 1% solid) of FSH bead was spiked into the test sample containing approximately 500 mIU/mL FSH, mixed vertically with pipette and immediately injected into the cartridge sample inlet. The beads can also be printed onto the sample inlet of the cartridge and dissolved into the sample later as the sample is introduced into the cartridge.

Example 9

LH Magnetic Bead Preparation

LH magnetic beads were prepared similar to Example 8 above except that Biospacific LH 5304 monoclonal antibody was used in place of Anti-FSH 95784.

Example 10

TSH Bead Preparation

TSH 5409ANA beads were prepared as follows: 15 mg of 0.2 μm carboxylated microparticles (10% weight/volume) (part#13000550100390, Seradyn, Indianapolis, Ind., USA), were reacted with 1.2 mg of TSH 5409 mAb in 25 mM 2-(N-morpholino)ethanesulfonic acid (IVIES buffer, pH 6.2) for 15 minutes, and then were centrifuged to remove the supernatant. After resuspension of the pellet in 25 mM IVIES buffer, 10 mM carbodiimide (EDAC) was added to the sample and reacted for 2 hours at 4° C. This was followed by centrifuging the sample, washing the pellet with ⅕ physiological phosphate buffer twice. A formulated sample with 3.2% solids in ⅕ physiological phosphate buffer, including a protein stabilization solution (Cat#Q2030529P1, Gwent Group, Pontypool, United Kingdom) was stored for further use. These beads were printed on chips used to build TSH cartridges.

TSH reference bead preparation was as follows: The process was the same as 5409ANA bead process except using anti-HSA antibody (HyTest Ltd, Cat 4T24 Mab 1C8, Joukahaisenkatu, Turku, Finland) in the reaction instead of 5409 mAb. The use of reference beads in immunosensor manufacture and operation is described in U.S. Pat. No. 7,732,099, the entirety of which is incorporated herein by reference. Here, an immuno-reference sensor is used to subtract a signal arising from non-specific binding of the signal antibody to the immunosensor.

Example 11A

TSH Signal Antibody Conjugate Synthesis

A preferred embodiment of the signal antibody conjugate synthesis is as follows: TSH T25C conjugate preparation used pepsin digested T25C whole antibody to make T25C F(ab)2' in 0.1M Citrate Buffer (pH 3.5) at 37° C. Purification of the T25C F(ab)2' fraction was done by using a S-300 size exclusion column (GE Healthcare, SE-751 84 Uppsala, Sweden). Monoethanolamine hydrochloride (MEA) was used to reduce T25C F(ab)₂' to Fab-SH, which was then reacted with LC-SMCC (Succinimidyl-4-[N-Maleimidomethyl]cyclohexane-1-carboxy-[6-amidocaproate]) and activated single molecule ALP (alkaline phosphatase) at 4° C. overnight. A size exclusion column was then used to purify the conjugate fraction and formulate it into a ⅕ physiological phosphate-buffered protein stabilization solution. This was then stored frozen at −80° C. for further use.

Example 11B

LH and FSH Signal Antibody Conjugate Synthesis

For the FSH and LH experiments, the 414B antibody recognizing the alpha-subunit was replaced with T25C described in Example 11A, above. This antibody was used for the scavenger bead experiments as the detection antibody.

Example 12

Scavenger or Sacrificial Beads

Figure 9:
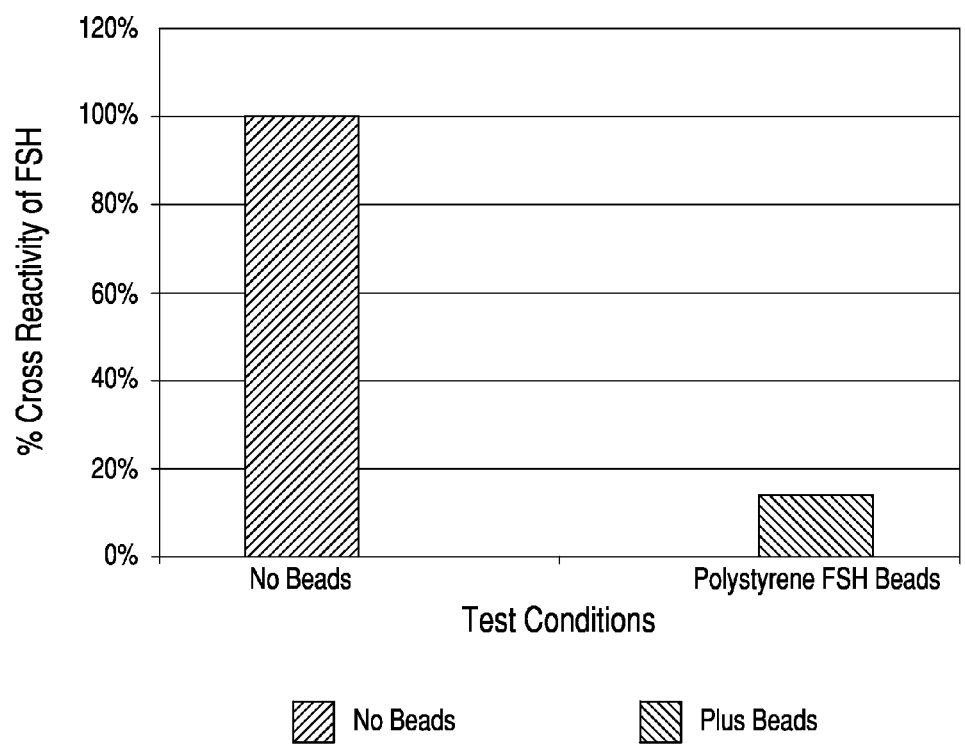
FIG. 9 is a graph showing reduced cross-reactivity of FSH using polystyrene beads.
Figure 10:
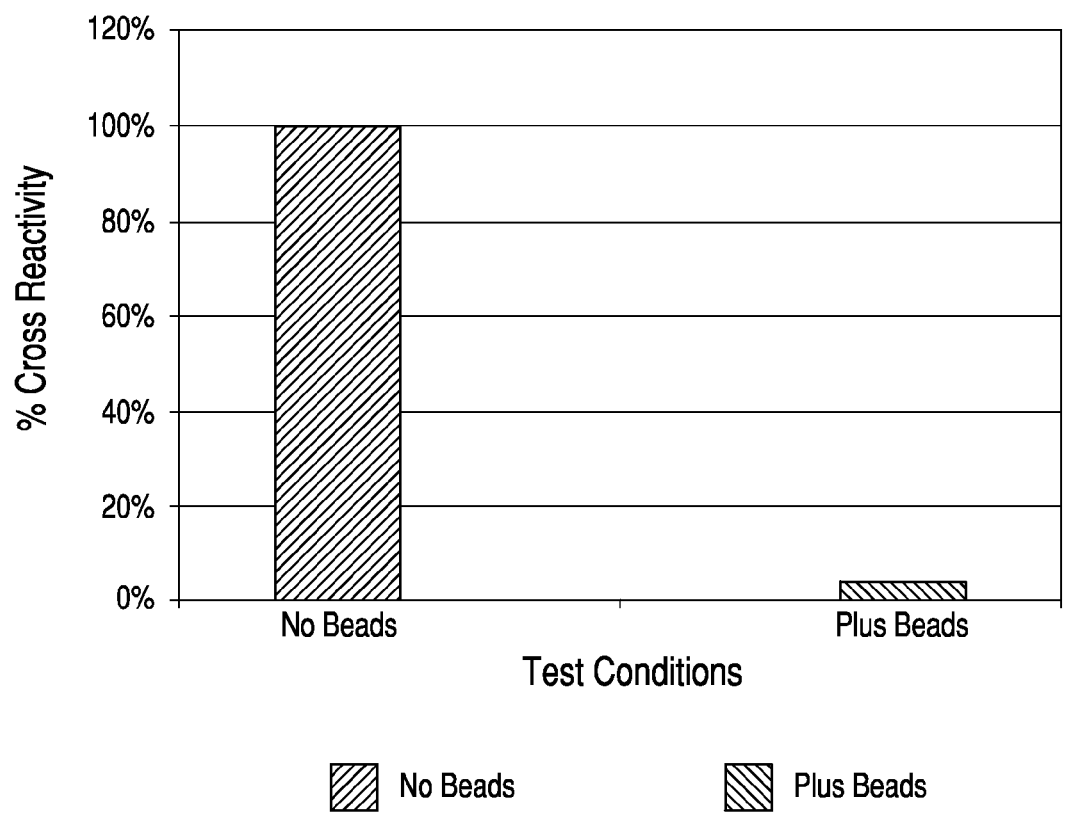
FIG. 10 is a graph showing reduced cross-reactivity of LH using polystyrene beads.
Figure 11:
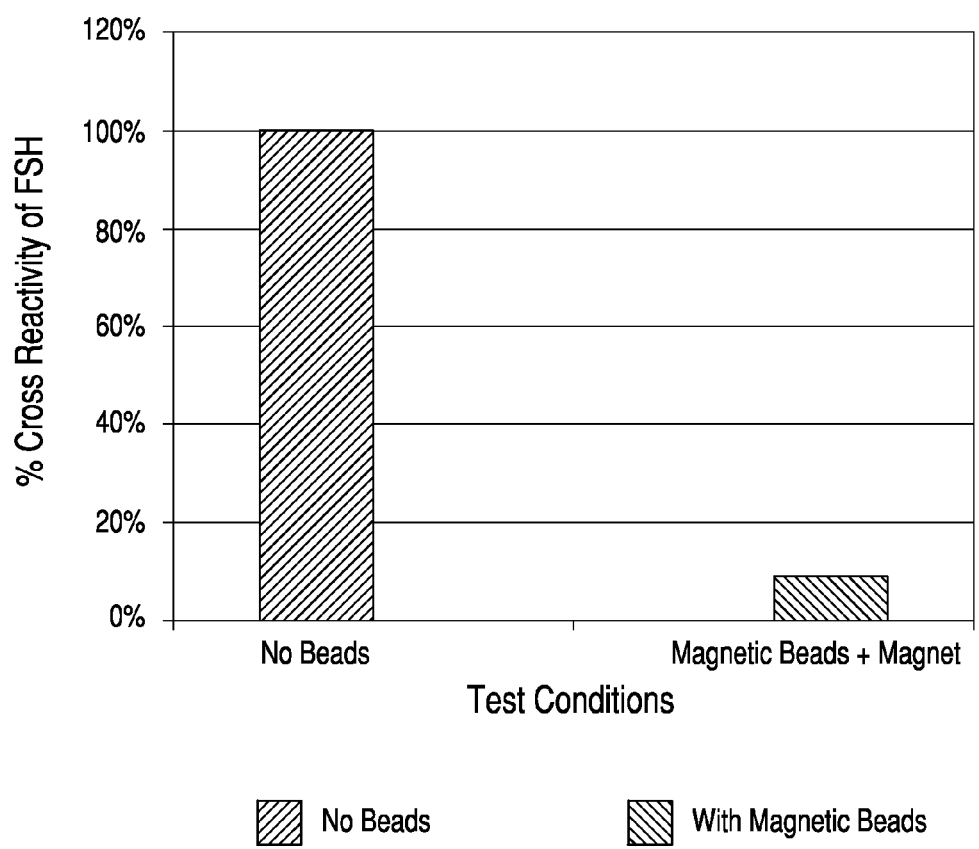
FIG. 11 is a graph showing reduced cross-reactivity of FSH using magnetic beads.

The utility of the scavenger bead approach is shown in FIGS. 9-11. As shown in FIG. 9, the use of polystyrene beads significantly reduced FSH interference from more than 100% cross reactivity to less than 15%. FIG. 9 is an experiment wherein FSH beads (Example 6) are built into FSH detecting cartridges. The sample contains extremely high concentrations (500 mIU/mL) of FSH. The signal with no addition of FSH scavenger beads was assigned a value of 100%. After the addition of FSH scavenger beads, the signal was reduced to 15%.

FIG. 10 focuses on the effect of LH scavenger beads from example 7. For the antibody combination LH capture and 414B described in Examples 7 and 11B, the LH cross-reactivity is 100% without the scavenger beads, whereas adding the scavenger beads to the assay cycle reduces the interference to 4%.

In the foregoing example, the LH antibody was the monoclonal antibody mus beta-LH, Catalog #5304 SP-5. Approximately 0.5 mg/mL, of beads were used. The FSH mAb was Anti-FSH 95784 SP-5. Table 13, below, provides additional information concerning various commercially available materials that may be employed as scavenger beads according to this embodiment of the invention.

TABLE 13

Commercially Available Antibodies

| Company | Cat# | Species | Type | Clone | Immunogen | Epitope | Use As |
| --- | --- | --- | --- | --- | --- | --- | --- |
| Biospacific | Anti-FSH 95784 SP-5 | *Mus* | mAb IgG1 | N/A | N/A | Beta-FSH | Scavenger |
| Biospacific | 5304 SP-5 | *Mus* | mAb IgG1 | N/A | N/A | Beta-LH | Scavenger |

TABLE 13-continued

Commercially Available Antibodies

| Company | Cat# | Species | Type | Clone | Immunogen | Epitope | Use As |
|---|---|---|---|---|---|---|---|
| Seradyn | MIT0414B | Mus | mAb IgG1 | BB3.1.3 | Human Luteinizing Hormone | Alpha Subunits | Signal |
| Abbott Diagnostics Division | 95784 | N/A | N/A | N/A | N/A | Beta-FSH | Scavenger |

FIG. 11 illustrates a significant reduction in FSH cross reactivity of from about 100% to less than 10% by employing magnetic beads. In this experiment, FSH detecting cartridges were built containing FSH polystyrene capture beads (Example 6), a Nickel coated ($Nd_2Fe_4B$) permanent magnet was built into the cartridge as shown in FIG. 8. Also, super paramagnetic FSH scavenger beads (Example 8) were printed on the sample inlet port (FIG. 5 sample inlet). With these component modifications, the cartridge was built similar to the standard procedures. The experiment was executed by adding approximately 20 μL of Abbott Architect 0 TSH Calibrator (Chicago, Ill.) sample spiked with 500 mIU/mL, of FSH.

The analyzer executed the steps in the assay with the cartridge and the resulting current generated in the assay was converted to 100% for the no scavenger bead cartridge test, and the sample with scavenger beads printed in the cartridge was calculated based on the no scavenger bead result, showing a significant reduction in signal, confirming the capability of the scavenger beads to reduce background in the assay.

Example 13

Screening for Substitute Monoclonal Antibody

As an alternative embodiment, eleven antibody preparations were obtained from a stock of TSH antibody cell lines at Abbott Diagnostic Division (ADD) as potential substitutes for the T25C and/or 5409 antibodies. The screening approach for a potential substitute monoclonal antibody to replace the T25C and/or 5409 antibodies was based on the hypothesis that if the same epitope was found in the uncharacterized antibody, that they should potentially possess similar properties to the T25C and/or 5409 antibodies.

TABLE 14

CANDIDATE ANTIBODIES FOR SUBSTITUTION

| Vendor | ID | Ab Epitope |
|---|---|---|
| Abbott Diagnostics Division | Clone 10-542-594 | N/A |
| Abbott Diagnostics Division | Clone 10-1064-137 | 5409 |
| Abbott Diagnostics Division | Clone10-1332-190 | N/A |
| Abbott Diagnostics Division | Clone10-541-173 | N/A |
| Abbott Diagnostics Division | Clone10-518-308 | 5409 |
| Abbott Diagnostics Division | Clone10-880-320 | 5409 |
| Abbott Diagnostics Division | Clone10-755-148 | 5409 |
| Abbott Diagnostics Division | Clone10-1179-456 | T25C |
| Abbott Diagnostics Division | Clone10-266-130 | 5409 |
| Abbott Diagnostics Division | Clone10-529-114 | 5409 |
| Abbott Diagnostics Division | Clone10-542-219 | N/A |

Approximately 0.1 ug ADD TSH whole mAb candidates were spiken along with 39 mIU/L TSH sample, mixed well and tested on the i-STAT® immunoassay cartridges with 5409 as the capture antibody and the T25C as the label antibody. Two antibody clones, 10-518-308 and 10-1179-45 (Table 14) demonstrated significant decrease of the detection signal, which indicated that they were competing with either the 5409 or the T25C antibody.

Once the antibody clones 10-518-308 and 10-1179-45 were identified as potential replacements for 5409 and/or T25C, the next testing step was to make beads and conjugate out of the monoclonal antibodies and to determine if they would form a usable sandwich (compatible antibody epitope pair) and determine whether they exhibited a good signal with TSH, and good selectivity against FSH, LH and CG.

The ADD TSH antibody 10-518-308 was made into ANA beads, printed on a sensor and built into no conjugate cartridges. The ADD TSH 10-1179-45 was digested into F(ab)2', reduced to Fab fragment and further conjugated with ALP to form the conjugate for the cartridge test. A 5409 ANA and T25C conjugate were used as control for performance comparison. There are four cartridge combinations for the following step in the evaluation.

TABLE 15

ANTIBODY COMBINATIONS TESTED IN i-STAT ® CARTRIDGES

| Combination # | ANA Beads | Conjugate |
|---|---|---|
| 1 | 5409 | T25C |
| 2 | 5409 | 10-1179-45 |
| 3 | 10-518-308 | T25C |
| 4 | 10-518-308 | 10-1179-45 |

These four sublots of cartridges (Table 15) were tested against a series of TSH in-house controls including stripped TSH plasma, at 0.1, 0.4, 0.6, 1, 8, 45, 88 mIU/L levels for the sensitivity and linearity evaluation. They were also tested against spiked LH, FSH at 500 mIU/ml and CG at 200000 mIU/ml in 0.4 mIU/L TSH samples for the cross-reactivity evaluation.

Based on the above tests, the TSH antibody clone 10-1179-456 was confirmed to be a potential candidate as replacing the Fitzgerald T25C antibody to pair with the antibody Biospacific 5409 as this combination has similar signal response to TSH and less than 10% cross-reactivity with LH, FSH and CG cross-reactants compared to the T25C/5409 combination.

While the invention has been described in terms of various preferred embodiments, those skilled in the art will recognize that various modifications, substitutions, omissions and changes can be made without departing from the spirit of the present invention. Accordingly, it is intended that the scope of the present invention be limited solely by the scope of the following claims.

What is claimed is:

1. A method for performing a thyroid stimulating hormone (TSH) immunoassay, the method comprising the steps of:

(a) inserting a fluid sample into a device comprising an immunosensor in a conduit, said immunosensor having a capture antibody specific for TSH immobilized thereon;
(b) dissolving a signal antibody into said fluid sample;
(c) forming a sandwich complex on said immunosensor, said complex comprising said capture antibody, TSH from the fluid sample, and said dissolved signal antibody;
(d) washing uncomplexed signal antibody and fluid sample from the immunosensor with a wash fluid in no more than one washing step; and
(e) detecting a signal associated with said complexed signal antibody as indicative of a level of TSH in the fluid sample;
wherein the capture antibody and the signal antibody are epitope-compatible antibodies;
wherein the capture antibody and the signal antibody, respectively, are capable of binding to at least two different epitopes on a TSH-β subunit of TSH;
wherein the capture antibody and the signal antibody each have a dissociation constant (Kd) for TSH;
wherein the capture antibody Kd for follicle stimulating hormone (FSH), luteinizing hormone (LH) and chorionic gonadotropin (CG) is in the range of from 70 to 1000 nM, 35 to 1000 nM and 40 to 500 nM, respectively;
wherein the signal antibody Kd for FSH, LH and CG is in the range of from 70 to 300 nM, 35 to 54 nM and 40 to 45, respectively;
wherein the capture antibody Kd for FSH, LH and CG is greater than the signal antibody Kd for FSH, LH and CG; and
wherein the capture antibody comprises mouse monoclonal anti-TSH-β antibody 5409 and the signal antibody comprises mouse monoclonal anti-TSH-β antibody M94206.

2. The method of claim 1, wherein the capture antibody has a first Kd ratio, Kd(FSH):Kd(TSH), that is in the range of from 1500 to 10000, and the signal antibody has a second Kd ratio, Kd(FSH):Kd(TSH), that is in the range of from 1500 to 3750.

3. The method of claim 1, wherein the sandwich complex is formed by substantially non-sequential contact of said capture and signal antibodies with the fluid sample.

4. The method of claim 1, wherein the sandwich complex is formed without one or more intervening wash steps directed to ameliorating a cross reaction with one or more of FSH, LH or CG.

5. The method of claim 1, wherein the fluid sample is a diluted blood sample, an undiluted blood sample, a diluted plasma sample, or an undiluted plasma sample.

6. The method of claim 1, wherein the capture antibody is covalently bound to a bead.

7. The method of claim 1, wherein the signal antibody is conjugated to a reporter molecule selected from the group consisting of alkaline phosphatase, horseradish peroxidase and a fluorescent moiety.

8. The method of claim 1, wherein the detecting step is electrochemical.

9. The method of claim 1, wherein the detecting step is optical.

10. The method of claim 1, wherein the wash fluid also comprises a substrate for a reporter molecule.

11. The method of claim 1, further comprising metering the fluid sample in a metering chamber to form a metered sample having a volume of from 1 to 500 μL.

12. The method of claim 1, further comprising bursting a wash fluid pouch, which is in fluid communication with the immunosensor, to release from 5 to 500 μL of wash fluid into said conduit for the washing step (d).

13. The method of claim 1, further comprising forming a plurality of air segments in said wash fluid.

14. A method for performing a thyroid stimulating hormone (TSH) immunoassay, the method comprising the steps of:
(a) inserting a fluid sample into a device comprising an immunosensor in a conduit, said immunosensor having a capture antibody specific for TSH immobilized thereon;
(b) dissolving a signal antibody into said fluid sample;
(c) forming a sandwich complex on said immunosensor, said complex comprising said capture antibody, TSH from the fluid sample, and said dissolved signal antibody;
(d) washing uncomplexed signal antibody and fluid sample from the immunosensor with a wash fluid in no more than one washing step; and
(e) detecting a signal associated with said complexed signal antibody as indicative of a level of TSH in the fluid sample;
wherein the capture antibody and the signal antibody are epitope-compatible antibodies;
wherein the capture antibody and the signal antibody, respectively, are capable of binding to at least two different epitopes on a TSH-β subunit of TSH;
wherein the capture antibody and the signal antibody each have a dissociation constant (Kd) for TSH;
wherein the capture antibody Kd for follicle stimulating hormone (FSH), luteinizing hormone (LH) and chorionic gonadotropin (CG) is in the range of from 70 to 1000 nM, 35 to 1000 nM and 40 to 500 nM, respectively;
wherein the signal antibody Kd for FSH, LH and CG is in the range of from 70 to 300 nM, 35 to 54 nM and 40 to 45, respectively;
wherein the capture antibody Kd for FSH, LH and CG is greater than the signal antibody Kd for FSH, LH and CG; and
wherein the capture antibody comprises mouse monoclonal anti-TSH-β antibody 5409 and the signal antibody comprises mouse monoclonal anti-TSH-β antibody Ab9390.

* * * * *